US009132063B2

(12) United States Patent
Lev et al.

(10) Patent No.: US 9,132,063 B2
(45) **Date of Patent: *Sep. 15, 2015**

(54) INLINE LIQUID DRUG MEDICAL DEVICES WITH LINEAR DISPLACEABLE SLIDING FLOW CONTROL MEMBER

(71) Applicant: MEDIMOP Medical Projects Ltd., Ra'anana (IL)

(72) Inventors: Nimrod Lev, Savion (IL); Igor Denenburg, Gedera (IL); Moshe Gilboa, Kfar Saba (IL)

(73) Assignee: Medimop Medical Projects Ltd., Ra'anana (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/504,979

(22) Filed: Oct. 2, 2014

(65) Prior Publication Data

US 2015/0020920 A1 Jan. 22, 2015

Related U.S. Application Data

(63) Continuation of application No. 13/505,881, filed as application No. PCT/IL2010/000915 on Nov. 4, 2010, now Pat. No. 8,979,792.

(30) Foreign Application Priority Data

Nov. 12, 2009 (IL) .......................................... 202070

(51) Int. Cl.
*A61J 1/20* (2006.01)
*A61M 37/00* (2006.01)
(Continued)

(52) U.S. Cl.
CPC .............. *A61J 1/2096* (2013.01); *A61J 1/2089* (2013.01); *B65B 3/003* (2013.01); *A61J 1/1418* (2015.05);

(Continued)

(58) Field of Classification Search
CPC ... A61M 1/2096; A61M 1/20; A61M 1/2089; A61M 1/2093; A61M 1/22; A61M 2001/2013; A61M 39/223; A61M 39/22; A61M 2039/224; A61M 2039/1077; B65B 3/003
USPC ...................................................... 604/80–87
See application file for complete search history.

(56) References Cited

U.S. PATENT DOCUMENTS

| | | | |
|---|---|---|---|
| 62,333 | A | 2/1867 | Holl |
| 1,021,681 | A | 3/1912 | Jennings |

(Continued)

FOREIGN PATENT DOCUMENTS

| | | | |
|---|---|---|---|
| CN | 1950049 | A | 4/2007 |
| DE | 1913926 | A1 | 9/1970 |

(Continued)

OTHER PUBLICATIONS

U.S. Appl. No. 14/391,792 by Lev, filed Oct. 10, 2014.

(Continued)

*Primary Examiner* — Quynh-Nhu H Vu
*Assistant Examiner* — Jenna Zhang
(74) *Attorney, Agent, or Firm* — Panitch Schwarze Belisario & Nadel LLP

(57) ABSTRACT

Inline liquid drug medical device having a longitudinal device axis, a housing with a linear displaceable sliding flow control member displaceable along a transverse bore from a first flow control position for establishing flow communication between a first pair of ports for liquid drug reconstitution purposes to a second flow control position for establishing flow communication between a second pair of ports for liquid drug administration purposes, and a manually operated actuating mechanism for applying a linear displacement force for urging the flow control member to slide along the bore from its first flow control position to its second flow control position.

15 Claims, 18 Drawing Sheets

(51) Int. Cl.
*A61M 5/32* (2006.01)
*B65B 3/00* (2006.01)

(52) U.S. Cl.
CPC ................ *A61J 1/201* (2015.05); *A61J 1/2013* (2015.05); *A61J 1/2062* (2015.05); *A61J 2001/201* (2013.01); *A61J 2001/2013* (2013.01); *A61J 2001/2062* (2013.01)

(56) References Cited

U.S. PATENT DOCUMENTS

| | | | | |
|---|---|---|---|---|
| 1,704,817 | A | 3/1929 | Ayers | |
| 1,930,944 | A | 10/1933 | Schmitz, Jr. | |
| 2,326,490 | A | 8/1943 | Perelson | |
| 2,931,668 | A | 4/1960 | Baley | |
| 2,968,497 | A | 1/1961 | Treleman | |
| 3,059,643 | A | 10/1962 | Barton | |
| D198,499 | S | 6/1964 | Harautuneian | |
| 3,225,763 | A | 12/1965 | Waterman | |
| 3,484,849 | A | 12/1969 | Huebner et al. | |
| 3,618,637 | A | 11/1971 | Santomieri | |
| 3,757,981 | A | 9/1973 | Harris, Sr. et al. | |
| 3,788,524 | A | 1/1974 | Davis et al. | |
| 3,822,700 | A | 7/1974 | Pennington | |
| 3,826,261 | A | 7/1974 | Killinger | |
| 3,872,992 | A | 3/1975 | Larson | |
| 3,885,607 | A | 5/1975 | Peltier | |
| 3,938,520 | A | 2/1976 | Scislowicz et al. | |
| 3,957,052 | A | 5/1976 | Topham | |
| 3,977,555 | A | 8/1976 | Larson | |
| 3,993,063 | A | 11/1976 | Larrabee | |
| 4,020,839 | A | 5/1977 | Klapp | |
| 4,051,852 | A | 10/1977 | Villari | |
| D248,568 | S | 7/1978 | Ismach | |
| 4,109,670 | A | 8/1978 | Slagel | |
| 4,121,585 | A | 10/1978 | Becker, Jr. | |
| 4,161,178 | A | 7/1979 | Genese | |
| 4,187,848 | A | 2/1980 | Taylor | |
| 4,203,067 | A | 5/1980 | Fitzky et al. | |
| 4,203,443 | A | 5/1980 | Genese | |
| 4,210,173 | A | 7/1980 | Choksi et al. | |
| D257,286 | S | 10/1980 | Folkman | |
| 4,253,501 | A | 3/1981 | Ogle | |
| 4,296,786 | A | 10/1981 | Brignola | |
| 4,303,067 | A | 12/1981 | Connolly et al. | |
| 4,312,349 | A | 1/1982 | Cohen | |
| 4,314,586 | A | 2/1982 | Folkman | |
| 4,328,802 | A | 5/1982 | Curley et al. | |
| 4,335,717 | A | 6/1982 | Bujan et al. | |
| D267,199 | S | 12/1982 | Koenig | |
| 4,376,634 | A | 3/1983 | Prior et al. | |
| D268,871 | S | 5/1983 | Benham et al. | |
| 4,392,850 | A | 7/1983 | Elias et al. | |
| D270,282 | S | 8/1983 | Gross | |
| 4,410,321 | A | 10/1983 | Pearson et al. | |
| 4,411,662 | A | 10/1983 | Pearson | |
| D271,421 | S | 11/1983 | Fetterman | |
| 4,434,823 | A | 3/1984 | Hudspith | |
| 4,465,471 | A | 8/1984 | Harris et al. | |
| 4,475,915 | A | 10/1984 | Sloane | |
| 4,493,348 | A | 1/1985 | Lemmons | |
| 4,505,709 | A | 3/1985 | Froning et al. | |
| 4,507,113 | A | 3/1985 | Dunlap | |
| D280,018 | S | 8/1985 | Scott | |
| 4,532,969 | A | 8/1985 | Kwaan | |
| 4,564,054 | A | 1/1986 | Gustavsson | |
| 4,573,993 | A | 3/1986 | Hoag et al. | |
| 4,576,211 | A | 3/1986 | Valentini et al. | |
| 4,581,014 | A | 4/1986 | Millerd et al. | |
| 4,588,396 | A | 5/1986 | Stroebel et al. | |
| 4,588,403 | A | 5/1986 | Weiss et al. | |
| D284,603 | S | 7/1986 | Loignon | |
| 4,604,093 | A | 8/1986 | Brown et al. | |
| 4,607,671 | A | 8/1986 | Aalto et al. | |
| 4,614,437 | A | 9/1986 | Buehler | |
| 4,638,975 | A | 1/1987 | Iuchi et al. | |
| 4,639,019 | A | 1/1987 | Mittleman | |
| 4,667,927 | A | 5/1987 | Oscarsson | |
| 4,676,530 | A | 6/1987 | Nordgren et al. | |
| 4,683,975 | A | 8/1987 | Booth et al. | |
| 4,697,622 | A | 10/1987 | Swift et al. | |
| 4,721,133 | A | 1/1988 | Sundblom | |
| 4,729,401 | A | 3/1988 | Raines | |
| 4,735,608 | A | 4/1988 | Sardam | |
| 4,743,229 | A | 5/1988 | Chu | |
| 4,743,243 | A | 5/1988 | Vaillancourt | |
| 4,752,292 | A | 6/1988 | Lopez et al. | |
| 4,758,235 | A | 7/1988 | Tu | |
| 4,759,756 | A | 7/1988 | Forman et al. | |
| 4,778,447 | A | 10/1988 | Velde et al. | |
| 4,787,898 | A | 11/1988 | Raines | |
| 4,797,898 | A | 1/1989 | Martinez | |
| 4,804,366 | A | 2/1989 | Zdeb et al. | |
| 4,832,690 | A | 5/1989 | Kuu | |
| 4,834,152 | A | 5/1989 | Howson et al. | |
| D303,013 | S | 8/1989 | Konopka | |
| 4,857,062 | A | 8/1989 | Russell | |
| 4,865,592 | A | 9/1989 | Rycroft | |
| 4,871,463 | A | 10/1989 | Taylor et al. | |
| 4,898,209 | A | 2/1990 | Zbed | |
| 4,909,290 | A | 3/1990 | Coccia | |
| 4,931,040 | A | 6/1990 | Haber et al. | |
| 4,932,944 | A | 6/1990 | Jagger et al. | |
| 4,967,797 | A | 11/1990 | Manska | |
| D314,050 | S | 1/1991 | Sone | |
| D314,622 | S | 2/1991 | Andersson et al. | |
| 4,997,430 | A | 3/1991 | Van der Heiden et al. | |
| 5,006,114 | A | 4/1991 | Rogers et al. | |
| 5,035,686 | A | 7/1991 | Crittenden et al. | |
| 5,041,105 | A | 8/1991 | D'Alo et al. | |
| 5,045,066 | A | 9/1991 | Scheuble et al. | |
| 5,049,129 | A | 9/1991 | Zdeb et al. | |
| 5,053,015 | A | 10/1991 | Gross | |
| 5,061,248 | A | 10/1991 | Sacco | |
| 5,088,996 | A | 2/1992 | Kopfer et al. | |
| 5,096,575 | A | 3/1992 | Cosack | |
| 5,104,387 | A | 4/1992 | Pokorney et al. | |
| 5,113,904 | A | 5/1992 | Aslanian | |
| 5,122,124 | A | 6/1992 | Novacek et al. | |
| 5,125,908 | A | 6/1992 | Cohen | |
| 5,125,915 | A | 6/1992 | Berry et al. | |
| D328,788 | S | 8/1992 | Sagae et al. | |
| 5,171,230 | A | 12/1992 | Eland et al. | |
| 5,201,705 | A | 4/1993 | Berglund et al. | |
| 5,201,717 | A * | 4/1993 | Wyatt et al. | 604/192 |
| 5,203,771 | A | 4/1993 | Melker et al. | |
| 5,203,775 | A | 4/1993 | Frank et al. | |
| 5,211,638 | A | 5/1993 | Dudar et al. | |
| 5,232,029 | A | 8/1993 | Knox et al. | |
| 5,232,109 | A | 8/1993 | Tirrell et al. | |
| 5,242,432 | A | 9/1993 | DeFrank | |
| 5,247,972 | A | 9/1993 | Tetreault | |
| D341,420 | S | 11/1993 | Conn | |
| 5,269,768 | A | 12/1993 | Cheung | |
| 5,270,219 | A | 12/1993 | DeCastro et al. | |
| 5,279,576 | A | 1/1994 | Loo et al. | |
| 5,288,290 | A | 2/1994 | Brody | |
| 5,300,034 | A | 4/1994 | Behnke et al. | |
| 5,301,685 | A | 4/1994 | Guirguis | |
| 5,304,163 | A | 4/1994 | Bonnici et al. | |
| 5,308,483 | A | 5/1994 | Sklar et al. | |
| 5,312,377 | A | 5/1994 | Dalton | |
| 5,328,474 | A | 7/1994 | Raines | |
| D349,648 | S | 8/1994 | Tirrell et al. | |
| 5,334,163 | A | 8/1994 | Sinnett | |
| 5,334,179 | A | 8/1994 | Poli et al. | |
| 5,342,346 | A | 8/1994 | Honda et al. | |
| 5,344,417 | A | 9/1994 | Wadsworth, Jr. | |
| 5,348,548 | A | 9/1994 | Meyer et al. | |
| 5,350,372 | A | 9/1994 | Ikeda et al. | |
| 5,364,386 | A | 11/1994 | Fukuoka et al. | |
| 5,364,387 | A | 11/1994 | Sweeney | |
| 5,374,264 | A | 12/1994 | Wadsworth, Jr. | |
| 5,385,547 | A | 1/1995 | Wong et al. | |

(56) References Cited

U.S. PATENT DOCUMENTS

| | | | |
|---|---|---|---|
| 5,397,303 | A | 3/1995 | Sancoff et al. |
| D357,733 | S | 4/1995 | Matkovich |
| 5,429,614 | A | 7/1995 | Fowles et al. |
| 5,433,330 | A | 7/1995 | Yatsko et al. |
| 5,445,630 | A | 8/1995 | Richmond |
| 5,445,631 | A | 8/1995 | Uchida |
| 5,451,374 | A | 9/1995 | Molina |
| 5,454,805 | A | 10/1995 | Brony |
| 5,464,111 | A | 11/1995 | Vacek et al. |
| 5,464,123 | A | 11/1995 | Scarrow |
| 5,466,219 | A | 11/1995 | Lynn et al. |
| 5,466,220 | A | 11/1995 | Brenneman |
| 5,470,327 | A | 11/1995 | Helgren et al. |
| 5,471,994 | A | 12/1995 | Guirguis |
| 5,472,022 | A | 12/1995 | Michel et al. |
| 5,478,337 | A | 12/1995 | Okamoto et al. |
| 5,492,147 | A | 2/1996 | Challender et al. |
| D369,406 | S | 4/1996 | Niedospial et al. |
| 5,505,714 | A | 4/1996 | Dassa et al. |
| 5,509,433 | A | 4/1996 | Paradis |
| 5,520,659 | A | 5/1996 | Hedges |
| 5,526,853 | A | 6/1996 | McPhee et al. |
| 5,527,306 | A | 6/1996 | Haining |
| 5,531,695 | A | 7/1996 | Swisher |
| 5,547,471 | A | 8/1996 | Thompson et al. |
| 5,549,577 | A | 8/1996 | Siegel et al. |
| 5,554,128 | A | 9/1996 | Hedges |
| 5,566,729 | A | 10/1996 | Grabenkort et al. |
| 5,569,191 | A | 10/1996 | Meyer |
| 5,573,281 | A | 11/1996 | Keller |
| 5,578,015 | A | 11/1996 | Robb |
| 5,583,052 | A | 12/1996 | Portnoff et al. |
| 5,584,819 | A | 12/1996 | Kopfer |
| 5,591,143 | A | 1/1997 | Trombley, III et al. |
| 5,603,706 | A | 2/1997 | Wyatt et al. |
| 5,607,439 | A | 3/1997 | Yoon |
| 5,611,576 | A | 3/1997 | Guala |
| 5,616,203 | A | 4/1997 | Stevens |
| 5,636,660 | A | 6/1997 | Pfleiderer et al. |
| 5,637,101 | A | 6/1997 | Shillington |
| 5,641,010 | A | 6/1997 | Maier |
| 5,645,538 | A | 7/1997 | Richmond |
| 5,647,845 | A | 7/1997 | Haber et al. |
| 5,651,776 | A | 7/1997 | Appling et al. |
| 5,653,686 | A | 8/1997 | Coulter et al. |
| 5,674,195 | A | 10/1997 | Truthan |
| 5,676,346 | A | 10/1997 | Leinsing |
| 5,685,845 | A | 11/1997 | Grimard |
| D388,172 | S | 12/1997 | Cipes |
| 5,699,821 | A | 12/1997 | Paradis |
| 5,702,019 | A | 12/1997 | Grimard |
| 5,718,346 | A | 2/1998 | Weiler |
| D393,722 | S | 4/1998 | Fangrow, Jr. et al. |
| 5,738,144 | A | 4/1998 | Rogers |
| 5,743,312 | A | 4/1998 | Pfeifer et al. |
| 5,746,733 | A | 5/1998 | Capaccio et al. |
| 5,755,696 | A | 5/1998 | Caizza |
| 5,766,211 | A | 6/1998 | Wood et al. |
| 5,772,630 | A | 6/1998 | Ljungquist |
| 5,772,652 | A | 6/1998 | Zielinski |
| RE35,841 | E | 7/1998 | Frank et al. |
| 5,776,116 | A | 7/1998 | Lopez et al. |
| 5,782,872 | A | 7/1998 | Muller |
| 5,806,831 | A | 9/1998 | Paradis |
| 5,810,792 | A | 9/1998 | Fangrow, Jr. et al. |
| D399,559 | S | 10/1998 | Molina |
| 5,817,082 | A | 10/1998 | Niedospial, Jr. et al. |
| 5,820,621 | A | 10/1998 | Yale et al. |
| 5,827,262 | A | 10/1998 | Neftel et al. |
| 5,832,971 | A | 11/1998 | Yale et al. |
| 5,833,213 | A | 11/1998 | Ryan |
| 5,834,744 | A | 11/1998 | Risman |
| 5,839,715 | A | 11/1998 | Leinsing |
| 5,853,406 | A | 12/1998 | Masuda et al. |
| D405,522 | S | 2/1999 | Hoenig et al. |
| 5,871,110 | A | 2/1999 | Grimard et al. |
| 5,873,872 | A | 2/1999 | Thibault et al. |
| 5,879,337 | A | 3/1999 | Kuracina et al. |
| 5,879,345 | A | 3/1999 | Aneas |
| 5,887,633 | A | 3/1999 | Yale et al. |
| 5,890,610 | A | 4/1999 | Jansen et al. |
| 5,891,129 | A | 4/1999 | Daubert et al. |
| 5,893,397 | A | 4/1999 | Peterson et al. |
| 5,897,526 | A | 4/1999 | Vaillancourt |
| 5,899,468 | A | 5/1999 | Apps et al. |
| 5,902,280 | A | 5/1999 | Powles et al. |
| 5,902,298 | A | 5/1999 | Niedospial, Jr. et al. |
| D410,740 | S | 6/1999 | Molina |
| 5,911,710 | A | 6/1999 | Barry et al. |
| 5,919,182 | A | 7/1999 | Avallone |
| 5,921,419 | A | 7/1999 | Niedospial, Jr. et al. |
| 5,924,584 | A | 7/1999 | Hellstrom et al. |
| 5,925,029 | A | 7/1999 | Jansen et al. |
| 5,935,112 | A | 8/1999 | Stevens et al. |
| 5,941,848 | A | 8/1999 | Nishimoto et al. |
| 5,944,700 | A | 8/1999 | Nguyen et al. |
| 5,954,104 | A | 9/1999 | Daubert et al. |
| 5,971,181 | A | 10/1999 | Niedospial, Jr. et al. |
| 5,971,965 | A | 10/1999 | Mayer |
| 5,989,237 | A | 11/1999 | Fowles et al. |
| 6,003,566 | A | 12/1999 | Thibault et al. |
| 6,004,278 | A | 12/1999 | Botich et al. |
| 6,019,750 | A | 2/2000 | Fowles et al. |
| 6,022,339 | A | 2/2000 | Fowles et al. |
| 6,036,171 | A | 3/2000 | Weinheimer et al. |
| 6,039,093 | A | 3/2000 | Mrotzek et al. |
| 6,039,302 | A | 3/2000 | Cote, Sr. et al. |
| D422,357 | S | 4/2000 | Niedospial, Jr. et al. |
| 6,063,068 | A | 5/2000 | Fowles et al. |
| D427,308 | S | 6/2000 | Zinger |
| D427,309 | S | 6/2000 | Molina |
| 6,070,623 | A | 6/2000 | Aneas |
| 6,071,270 | A | 6/2000 | Fowles et al. |
| 6,080,132 | A | 6/2000 | Cole et al. |
| D428,141 | S | 7/2000 | Brotspies et al. |
| 6,086,762 | A | 7/2000 | Guala |
| 6,089,541 | A | 7/2000 | Weinheimer et al. |
| 6,090,091 | A | 7/2000 | Fowles et al. |
| 6,090,093 | A | 7/2000 | Thibault et al. |
| 6,092,692 | A | 7/2000 | Riskin |
| D430,291 | S | 8/2000 | Jansen et al. |
| 6,099,511 | A | 8/2000 | Devos et al. |
| 6,113,068 | A | 9/2000 | Ryan |
| 6,113,583 | A | 9/2000 | Fowles et al. |
| 6,117,114 | A | 9/2000 | Paradis |
| 6,139,534 | A | 10/2000 | Niedospial, Jr. et al. |
| 6,142,446 | A | 11/2000 | Leinsing |
| 6,146,362 | A | 11/2000 | Turnbull et al. |
| 6,149,623 | A | 11/2000 | Reynolds |
| 6,156,025 | A | 12/2000 | Niedospial, Jr. et al. |
| 6,159,192 | A | 12/2000 | Fowles et al. |
| 6,168,037 | B1 | 1/2001 | Grimard |
| 6,171,287 | B1 | 1/2001 | Lynn et al. |
| 6,171,293 | B1 | 1/2001 | Rowley et al. |
| 6,173,852 | B1 | 1/2001 | Browne |
| 6,173,868 | B1 | 1/2001 | DeJonge |
| 6,174,304 | B1 | 1/2001 | Weston |
| 6,179,822 | B1 | 1/2001 | Niedospial, Jr. |
| 6,179,823 | B1 | 1/2001 | Niedospial, Jr. |
| 6,206,861 | B1 | 3/2001 | Mayer |
| 6,221,041 | B1 | 4/2001 | Russo |
| 6,221,054 | B1 | 4/2001 | Martin et al. |
| 6,221,065 | B1 | 4/2001 | Davis |
| 6,238,372 | B1 | 5/2001 | Zinger et al. |
| 6,245,044 | B1 | 6/2001 | Daw et al. |
| D445,501 | S | 7/2001 | Niedospial, Jr. |
| D445,895 | S | 7/2001 | Svendsen |
| 6,253,804 | B1 | 7/2001 | Safabash |
| 6,258,078 | B1 | 7/2001 | Thilly |
| 6,280,430 | B1 | 8/2001 | Neftel et al. |
| 6,290,688 | B1 | 9/2001 | Lopez et al. |
| 6,296,621 | B1 | 10/2001 | Masuda et al. |
| 6,299,131 | B1 | 10/2001 | Ryan |
| 6,343,629 | B1 | 2/2002 | Wessman et al. |

(56) References Cited

U.S. PATENT DOCUMENTS

| | | | | |
|---|---|---|---|---|
| 6,348,044 | B1 | 2/2002 | Coletti et al. | |
| 6,358,236 | B1 | 3/2002 | DeFoggi et al. | |
| 6,364,866 | B1 | 4/2002 | Furr et al. | |
| 6,378,576 | B2 | 4/2002 | Thibault et al. | |
| 6,378,714 | B1 | 4/2002 | Jansen et al. | |
| 6,379,340 | B1 | 4/2002 | Zinger et al. | |
| 6,382,442 | B1 | 5/2002 | Thibault et al. | |
| 6,386,397 | B2 | 5/2002 | Brotspies et al. | |
| 6,408,897 | B1 | 6/2002 | Laurent et al. | |
| 6,409,708 | B1 | 6/2002 | Wessman | |
| 6,440,107 | B1 | 8/2002 | Trombley, III et al. | |
| 6,453,949 | B1 | 9/2002 | Chau | |
| 6,453,956 | B2 | 9/2002 | Safabash | |
| 6,474,375 | B2 | 11/2002 | Spero et al. | |
| 6,478,788 | B1 | 11/2002 | Aneas | |
| D468,015 | S | 12/2002 | Horppu | |
| 6,499,617 | B1 | 12/2002 | Niedospial, Jr. et al. | |
| 6,503,240 | B1 | 1/2003 | Niedospial, Jr. et al. | |
| 6,503,244 | B2 | 1/2003 | Hayman | |
| 6,520,932 | B2 | 2/2003 | Taylor | |
| 6,524,278 | B1 | 2/2003 | Campbell et al. | |
| 6,524,295 | B2 | 2/2003 | Daubert et al. | |
| D472,316 | S | 3/2003 | Douglas et al. | |
| 6,530,903 | B2 | 3/2003 | Wang et al. | |
| 6,537,263 | B1 | 3/2003 | Aneas | |
| D472,630 | S | 4/2003 | Douglas et al. | |
| 6,544,246 | B1 | 4/2003 | Niedospial, Jr. | |
| 6,551,299 | B2 | 4/2003 | Miyoshi et al. | |
| 6,558,365 | B2 | 5/2003 | Zinger et al. | |
| 6,571,837 | B2 | 6/2003 | Jansen et al. | |
| 6,572,591 | B2 | 6/2003 | Mayer | |
| 6,575,955 | B2 | 6/2003 | Azzolini | |
| 6,581,593 | B1 | 6/2003 | Rubin et al. | |
| 6,582,415 | B1 | 6/2003 | Fowles et al. | |
| D476,731 | S | 7/2003 | Cise et al. | |
| 6,591,876 | B2 | 7/2003 | Safabash | |
| 6,601,721 | B2 | 8/2003 | Jansen et al. | |
| 6,626,309 | B1 | 9/2003 | Jansen et al. | |
| 6,638,244 | B1 | 10/2003 | Reynolds | |
| D482,121 | S | 11/2003 | Harding et al. | |
| D482,447 | S | 11/2003 | Harding et al. | |
| 6,651,956 | B2 | 11/2003 | Miller | |
| 6,652,509 | B1 | 11/2003 | Helgren et al. | |
| D483,487 | S | 12/2003 | Harding et al. | |
| D483,869 | S | 12/2003 | Tran et al. | |
| 6,656,433 | B2 | 12/2003 | Sasso | |
| 6,666,852 | B2 | 12/2003 | Niedospial, Jr. | |
| 6,681,810 | B2 | 1/2004 | Weston | |
| 6,681,946 | B1 | 1/2004 | Jansen et al. | |
| 6,682,509 | B2 | 1/2004 | Lopez | |
| 6,692,478 | B1 | 2/2004 | Paradis | |
| 6,692,829 | B2 | 2/2004 | Stubler et al. | |
| 6,695,829 | B2 | 2/2004 | Hellstrom et al. | |
| 6,699,229 | B2 | 3/2004 | Zinger et al. | |
| 6,706,022 | B1 | 3/2004 | Leinsing et al. | |
| 6,706,031 | B2 | 3/2004 | Manera | |
| 6,715,520 | B2 | 4/2004 | Andreasson et al. | |
| 6,729,370 | B2 | 5/2004 | Norton et al. | |
| 6,736,798 | B2 | 5/2004 | Ohkubo et al. | |
| 6,745,998 | B2 | 6/2004 | Doyle | |
| 6,746,438 | B1 | 6/2004 | Arnissolle | |
| 6,752,180 | B2 | 6/2004 | Delay | |
| D495,416 | S | 8/2004 | Dimeo et al. | |
| D496,457 | S | 9/2004 | Prais et al. | |
| 6,802,490 | B2 | 10/2004 | Leinsing et al. | |
| 6,832,994 | B2 | 12/2004 | Niedospial, Jr. et al. | |
| 6,852,103 | B2 * | 2/2005 | Fowles et al. | 604/413 |
| 6,875,203 | B1 | 4/2005 | Fowles et al. | |
| 6,875,205 | B2 | 4/2005 | Leinsing | |
| 6,878,131 | B2 | 4/2005 | Novacek et al. | |
| 6,890,328 | B2 | 5/2005 | Fowles et al. | |
| D506,256 | S | 6/2005 | Miyoshi et al. | |
| 6,901,975 | B2 | 6/2005 | Aramata et al. | |
| 6,945,417 | B2 | 9/2005 | Jansen et al. | |
| 6,948,522 | B2 | 9/2005 | Newbrough et al. | |
| 6,949,086 | B2 | 9/2005 | Ferguson et al. | |
| 6,957,745 | B2 | 10/2005 | Thibault et al. | |
| RE38,996 | E | 2/2006 | Crawford et al. | |
| 6,994,315 | B2 | 2/2006 | Ryan et al. | |
| 6,997,916 | B2 | 2/2006 | Simas, Jr. et al. | |
| 6,997,917 | B2 | 2/2006 | Niedospial, Jr. et al. | |
| 7,024,968 | B2 | 4/2006 | Raudabough et al. | |
| 7,070,589 | B2 | 7/2006 | Lolachi et al. | |
| 7,074,216 | B2 | 7/2006 | Fowles et al. | |
| 7,083,600 | B2 | 8/2006 | Meloul | |
| 7,086,431 | B2 | 8/2006 | D'Antonio et al. | |
| 7,100,890 | B2 | 9/2006 | Cote, Sr. et al. | |
| 7,140,401 | B2 | 11/2006 | Wilcox et al. | |
| 7,150,735 | B2 | 12/2006 | Hickle | |
| 7,192,423 | B2 | 3/2007 | Wong | |
| 7,195,623 | B2 | 3/2007 | Burroughs et al. | |
| 7,241,285 | B1 | 7/2007 | Dikeman | |
| 7,294,122 | B2 | 11/2007 | Kubo et al. | |
| 7,306,199 | B2 | 12/2007 | Leinsing et al. | |
| D561,348 | S | 2/2008 | Zinger et al. | |
| 7,326,188 | B1 | 2/2008 | Russell et al. | |
| 7,326,194 | B2 | 2/2008 | Zinger et al. | |
| 7,350,764 | B2 | 4/2008 | Raybuck | |
| 7,354,422 | B2 | 4/2008 | Riesenberger et al. | |
| 7,354,427 | B2 | 4/2008 | Fangrow | |
| 7,425,209 | B2 | 9/2008 | Fowles et al. | |
| 7,435,246 | B2 | 10/2008 | Zihlmann | |
| 7,452,348 | B2 | 11/2008 | Hasegawa | |
| 7,470,257 | B2 | 12/2008 | Norton et al. | |
| 7,470,265 | B2 | 12/2008 | Brugger et al. | |
| 7,472,932 | B2 | 1/2009 | Weber et al. | |
| 7,488,297 | B2 | 2/2009 | Flaherty | |
| 7,491,197 | B2 | 2/2009 | Jansen et al. | |
| 7,497,848 | B2 | 3/2009 | Leinsing et al. | |
| 7,523,967 | B2 | 4/2009 | Steppe | |
| 7,530,546 | B2 | 5/2009 | Ryan et al. | |
| D595,420 | S | 6/2009 | Suzuki et al. | |
| D595,421 | S | 6/2009 | Suzuki et al. | |
| 7,540,863 | B2 | 6/2009 | Haindl | |
| 7,540,865 | B2 | 6/2009 | Griffin et al. | |
| 7,544,191 | B2 | 6/2009 | Peluso et al. | |
| D595,862 | S | 7/2009 | Suzuki et al. | |
| D595,863 | S | 7/2009 | Suzuki et al. | |
| 7,611,487 | B2 | 11/2009 | Woehr et al. | |
| 7,611,502 | B2 | 11/2009 | Daly | |
| 7,615,041 | B2 | 11/2009 | Sullivan et al. | |
| 7,628,779 | B2 | 12/2009 | Aneas | |
| 7,632,261 | B2 | 12/2009 | Zinger et al. | |
| D608,900 | S | 1/2010 | Giraud et al. | |
| 7,654,995 | B2 | 2/2010 | Warren et al. | |
| 7,670,326 | B2 | 3/2010 | Shemesh | |
| 7,695,445 | B2 | 4/2010 | Yuki | |
| D616,090 | S | 5/2010 | Kawamura | |
| 7,713,247 | B2 | 5/2010 | Lopez | |
| 7,717,886 | B2 | 5/2010 | Lopez | |
| 7,722,090 | B2 | 5/2010 | Burton et al. | |
| D616,984 | S | 6/2010 | Gilboa | |
| 7,731,678 | B2 | 6/2010 | Tennican et al. | |
| 7,743,799 | B2 | 6/2010 | Mosler et al. | |
| 7,744,581 | B2 | 6/2010 | Wallen et al. | |
| 7,757,901 | B2 | 7/2010 | Welp | |
| 7,758,082 | B2 | 7/2010 | Weigel et al. | |
| 7,762,524 | B2 | 7/2010 | Cawthon et al. | |
| 7,766,304 | B2 | 8/2010 | Phillips | |
| 7,771,383 | B2 | 8/2010 | Truitt et al. | |
| D624,641 | S | 9/2010 | Boclet | |
| 7,799,009 | B2 | 9/2010 | Niedospial, Jr. et al. | |
| 7,803,140 | B2 | 9/2010 | Fangrow, Jr. | |
| D627,216 | S | 11/2010 | Fulginiti | |
| D630,732 | S | 1/2011 | Lev et al. | |
| 7,862,537 | B2 | 1/2011 | Zinger et al. | |
| 7,867,215 | B2 | 1/2011 | Akerlund et al. | |
| 7,879,018 | B2 | 2/2011 | Zinger et al. | |
| D634,007 | S | 3/2011 | Zinger et al. | |
| 7,900,659 | B2 | 3/2011 | Whitley et al. | |
| D637,713 | S | 5/2011 | Nord et al. | |
| 7,985,216 | B2 | 7/2011 | Daily et al. | |
| D644,104 | S | 8/2011 | Maeda et al. | |
| 7,993,328 | B2 | 8/2011 | Whitley | |

(56) References Cited

U.S. PATENT DOCUMENTS

| | | | |
|---|---|---|---|
| 8,007,461 | B2 | 8/2011 | Huo et al. |
| 8,012,132 | B2 | 9/2011 | Lum et al. |
| 8,016,809 | B2 | 9/2011 | Zinger et al. |
| 8,021,325 | B2 | 9/2011 | Zinger et al. |
| 8,025,653 | B2 | 9/2011 | Capitaine et al. |
| 8,029,472 | B2 | 10/2011 | Leinsing et al. |
| 8,038,123 | B2 | 10/2011 | Ruschke et al. |
| 8,066,688 | B2 | 11/2011 | Zinger et al. |
| 8,070,739 | B2 | 12/2011 | Zinger et al. |
| 8,075,550 | B2 | 12/2011 | Nord et al. |
| 8,096,525 | B2 | 1/2012 | Ryan |
| 8,105,314 | B2 | 1/2012 | Fangrow, Jr. |
| D654,166 | S | 2/2012 | Lair |
| D655,017 | S | 2/2012 | Mosler et al. |
| 8,122,923 | B2 | 2/2012 | Kraus et al. |
| 8,123,736 | B2 | 2/2012 | Kraushaar et al. |
| 8,157,784 | B2 | 4/2012 | Rogers |
| 8,167,863 | B2 | 5/2012 | Yow |
| 8,172,824 | B2 | 5/2012 | Pfeifer et al. |
| 8,177,768 | B2 | 5/2012 | Leinsing |
| 8,182,452 | B2 | 5/2012 | Mansour et al. |
| 8,187,248 | B2 | 5/2012 | Zihlmann |
| 8,196,614 | B2 | 6/2012 | Kriheli |
| 8,197,459 | B2 | 6/2012 | Jansen et al. |
| 8,211,069 | B2 | 7/2012 | Fangrow, Jr. |
| 8,225,959 | B2 | 7/2012 | Lambrecht |
| 8,241,268 | B2 | 8/2012 | Whitley |
| 8,262,628 | B2 | 9/2012 | Fangrow, Jr. |
| 8,262,641 | B2 | 9/2012 | Vedrine et al. |
| 8,267,127 | B2 | 9/2012 | Kriheli |
| D669,980 | S | 10/2012 | Lev et al. |
| 8,287,513 | B2 | 10/2012 | Ellstrom et al. |
| D673,673 | S | 1/2013 | Wang |
| D674,088 | S | 1/2013 | Lev et al. |
| D681,230 | S | 4/2013 | Mosler et al. |
| 8,454,573 | B2 | 6/2013 | Wyatt et al. |
| 8,469,939 | B2 | 6/2013 | Fangrow, Jr. |
| 8,475,404 | B2 | 7/2013 | Foshee et al. |
| 8,480,645 | B1 | 7/2013 | Choudhury et al. |
| 8,480,646 | B2 | 7/2013 | Nord et al. |
| 8,506,548 | B2 | 8/2013 | Okiyama |
| 8,511,352 | B2 | 8/2013 | Kraus et al. |
| 8,512,309 | B2 | 8/2013 | Shemesh et al. |
| D690,418 | S | 9/2013 | Rosenquist |
| 8,523,837 | B2 | 9/2013 | Wiggins et al. |
| 8,545,476 | B2 | 10/2013 | Ariagno et al. |
| 8,551,067 | B2 | 10/2013 | Zinger et al. |
| 8,556,879 | B2 | 10/2013 | Okiyama |
| 8,562,582 | B2 | 10/2013 | Tuckwell et al. |
| 8,608,723 | B2 | 12/2013 | Lev et al. |
| 8,628,508 | B2 | 1/2014 | Weitzel et al. |
| 8,684,992 | B2 | 4/2014 | Sullivan et al. |
| 8,752,598 | B2 | 6/2014 | Denenburg et al. |
| D717,406 | S | 11/2014 | Stanley et al. |
| 8,900,212 | B2 | 12/2014 | Kubo |
| 2001/0000347 | A1 | 4/2001 | Hellstrom et al. |
| 2001/0025671 | A1 | 10/2001 | Safabash |
| 2001/0029360 | A1 | 10/2001 | Miyoshi et al. |
| 2001/0051793 | A1 | 12/2001 | Weston |
| 2002/0017328 | A1 | 2/2002 | Loo |
| 2002/0066715 | A1 | 6/2002 | Niedospial |
| 2002/0087118 | A1 | 7/2002 | Reynolds et al. |
| 2002/0087141 | A1 | 7/2002 | Zinger et al. |
| 2002/0087144 | A1 | 7/2002 | Zinger et al. |
| 2002/0121496 | A1 | 9/2002 | Thiebault et al. |
| 2002/0123736 | A1 | 9/2002 | Fowles et al. |
| 2002/0127150 | A1 | 9/2002 | Sasso |
| 2002/0128628 | A1 | 9/2002 | Fathallah |
| 2002/0138045 | A1 | 9/2002 | Moen |
| 2002/0173752 | A1 | 11/2002 | Polzin |
| 2002/0193777 | A1 | 12/2002 | Aneas |
| 2003/0028156 | A1 | 2/2003 | Juliar |
| 2003/0036725 | A1 | 2/2003 | Lavi et al. |
| 2003/0068354 | A1 | 4/2003 | Reif et al. |
| 2003/0073971 | A1 | 4/2003 | Saker |
| 2003/0100866 | A1 | 5/2003 | Reynolds |
| 2003/0109846 | A1 | 6/2003 | Zinger et al. |
| 2003/0120209 | A1 | 6/2003 | Jensen et al. |
| 2003/0153895 | A1 | 8/2003 | Leinsing |
| 2003/0187420 | A1 | 10/2003 | Akerlund et al. |
| 2003/0191445 | A1 | 10/2003 | Wallen et al. |
| 2003/0195479 | A1 | 10/2003 | Kuracina et al. |
| 2003/0199846 | A1 | 10/2003 | Fowles et al. |
| 2003/0199847 | A1 | 10/2003 | Akerlund et al. |
| 2004/0024354 | A1 | 2/2004 | Reynolds |
| 2004/0039365 | A1 | 2/2004 | Aramata et al. |
| 2004/0044327 | A1 | 3/2004 | Hasegawa |
| 2004/0073189 | A1 | 4/2004 | Wyatt et al. |
| 2004/0143226 | A1 | 7/2004 | Marsden |
| 2004/0153047 | A1 | 8/2004 | Blank et al. |
| 2004/0181192 | A1 | 9/2004 | Cuppy |
| 2004/0204699 | A1 | 10/2004 | Hanly et al. |
| 2004/0217315 | A1 | 11/2004 | Doyle |
| 2004/0225274 | A1* | 11/2004 | Jansen et al. .................. 604/411 |
| 2004/0236305 | A1 | 11/2004 | Jansen et al. |
| 2004/0255952 | A1 | 12/2004 | Carlsen et al. |
| 2005/0015070 | A1 | 1/2005 | Delnevo et al. |
| 2005/0016626 | A1 | 1/2005 | Wilcox et al. |
| 2005/0055008 | A1 | 3/2005 | Paradis et al. |
| 2005/0082828 | A1 | 4/2005 | Wicks et al. |
| 2005/0124964 | A1 | 6/2005 | Niedospial et al. |
| 2005/0137566 | A1 | 6/2005 | Fowles et al. |
| 2005/0148994 | A1 | 7/2005 | Leinsing |
| 2005/0159724 | A1 | 7/2005 | Enerson |
| 2005/0182383 | A1 | 8/2005 | Wallen |
| 2005/0209554 | A1 | 9/2005 | Landau |
| 2005/0261637 | A1 | 11/2005 | Miller |
| 2005/0277896 | A1 | 12/2005 | Messerli et al. |
| 2006/0030832 | A1 | 2/2006 | Niedospial et al. |
| 2006/0079834 | A1 | 4/2006 | Tennican et al. |
| 2006/0089594 | A1 | 4/2006 | Landau |
| 2006/0089603 | A1 | 4/2006 | Truitt et al. |
| 2006/0095015 | A1 | 5/2006 | Hobbs et al. |
| 2006/0106360 | A1 | 5/2006 | Wong |
| 2006/0135948 | A1 | 6/2006 | Varma |
| 2006/0155257 | A1 | 7/2006 | Reynolds |
| 2006/0253084 | A1 | 11/2006 | Nordgren |
| 2007/0024995 | A1 | 2/2007 | Hayashi |
| 2007/0060904 | A1 | 3/2007 | Vedrine et al. |
| 2007/0079894 | A1 | 4/2007 | Kraus et al. |
| 2007/0083164 | A1 | 4/2007 | Barrelle et al. |
| 2007/0088252 | A1 | 4/2007 | Pestotnik et al. |
| 2007/0088293 | A1 | 4/2007 | Fangrow |
| 2007/0088313 | A1 | 4/2007 | Zinger et al. |
| 2007/0106244 | A1 | 5/2007 | Mosler et al. |
| 2007/0112324 | A1 | 5/2007 | Hamedi-Sangsari |
| 2007/0156112 | A1 | 7/2007 | Walsh |
| 2007/0167904 | A1 | 7/2007 | Zinger et al. |
| 2007/0191760 | A1 | 8/2007 | Iguchi et al. |
| 2007/0191764 | A1 | 8/2007 | Zihlmann |
| 2007/0191767 | A1 | 8/2007 | Hennessy et al. |
| 2007/0203451 | A1 | 8/2007 | Murakami et al. |
| 2007/0219483 | A1 | 9/2007 | Kitani et al. |
| 2007/0244461 | A1 | 10/2007 | Fangrow |
| 2007/0244462 | A1 | 10/2007 | Fangrow |
| 2007/0244463 | A1 | 10/2007 | Warren et al. |
| 2007/0249995 | A1 | 10/2007 | Van Manen |
| 2007/0255202 | A1 | 11/2007 | Kitani et al. |
| 2007/0265574 | A1 | 11/2007 | Tennican et al. |
| 2007/0265581 | A1 | 11/2007 | Funamura et al. |
| 2007/0270778 | A9 | 11/2007 | Zinger et al. |
| 2007/0287953 | A1 | 12/2007 | Ziv et al. |
| 2007/0299404 | A1 | 12/2007 | Katoh et al. |
| 2008/0009789 | A1* | 1/2008 | Zinger et al. .................... 604/89 |
| 2008/0009822 | A1 | 1/2008 | Enerson |
| 2008/0135051 | A1 | 6/2008 | Lee |
| 2008/0172024 | A1 | 7/2008 | Yow |
| 2008/0188799 | A1 | 8/2008 | Mueller-Beckhaus et al. |
| 2008/0249479 | A1 | 10/2008 | Zinger et al. |
| 2008/0249498 | A1 | 10/2008 | Fangrow |
| 2008/0287905 | A1 | 11/2008 | Hiejima et al. |
| 2008/0294100 | A1 | 11/2008 | de Costa et al. |
| 2008/0306439 | A1 | 12/2008 | Nelson et al. |
| 2008/0312634 | A1 | 12/2008 | Helmerson et al. |

(56) References Cited

U.S. PATENT DOCUMENTS

| | | | |
|---|---|---|---|
| 2009/0012492 | A1 | 1/2009 | Zihlmann |
| 2009/0082750 | A1 | 3/2009 | Denenburg et al. |
| 2009/0143758 | A1 | 6/2009 | Okiyama |
| 2009/0177177 | A1 | 7/2009 | Zinger et al. |
| 2009/0177178 | A1 | 7/2009 | Pedersen |
| 2009/0187140 | A1 | 7/2009 | Racz |
| 2009/0216212 | A1 | 8/2009 | Fangrow, Jr. |
| 2009/0267011 | A1 | 10/2009 | Hatton et al. |
| 2009/0299325 | A1 | 12/2009 | Vedrine et al. |
| 2009/0326506 | A1 | 12/2009 | Hasegawa et al. |
| 2010/0010443 | A1 | 1/2010 | Morgan et al. |
| 2010/0022985 | A1 | 1/2010 | Sullivan et al. |
| 2010/0030181 | A1 | 2/2010 | Helle et al. |
| 2010/0036319 | A1 | 2/2010 | Drake et al. |
| 2010/0076397 | A1 | 3/2010 | Reed et al. |
| 2010/0087786 | A1 | 4/2010 | Zinger et al. |
| 2010/0137827 | A1 | 6/2010 | Warren et al. |
| 2010/0160889 | A1 | 6/2010 | Smith et al. |
| 2010/0168712 | A1 | 7/2010 | Tuckwell et al. |
| 2010/0179506 | A1 | 7/2010 | Shemesh et al. |
| 2010/0198148 | A1 | 8/2010 | Zinger et al. |
| 2010/0204670 | A1 | 8/2010 | Kraushaar et al. |
| 2010/0241088 | A1 | 9/2010 | Ranalletta et al. |
| 2010/0274184 | A1 | 10/2010 | Chun |
| 2010/0286661 | A1 | 11/2010 | Raday et al. |
| 2010/0312220 | A1 | 12/2010 | Kalitzki |
| 2011/0004184 | A1 | 1/2011 | Proksch et al. |
| 2011/0054440 | A1 | 3/2011 | Lewis |
| 2011/0087164 | A1 | 4/2011 | Mosler et al. |
| 2011/0160701 | A1 | 6/2011 | Wyatt et al. |
| 2011/0224640 | A1 | 9/2011 | Kuhn et al. |
| 2011/0230856 | A1 | 9/2011 | Kyle et al. |
| 2011/0264037 | A1 | 10/2011 | Foshee et al. |
| 2011/0264069 | A1 | 10/2011 | Bochenko |
| 2011/0276007 | A1 | 11/2011 | Denenburg |
| 2011/0319827 | A1 | 12/2011 | Leinsing et al. |
| 2012/0022469 | A1 | 1/2012 | Alpert |
| 2012/0053555 | A1 | 3/2012 | Ariagno et al. |
| 2012/0059346 | A1 | 3/2012 | Sheppard et al. |
| 2012/0067429 | A1 | 3/2012 | Mosler et al. |
| 2012/0078214 | A1 | 3/2012 | Finke et al. |
| 2012/0123382 | A1 | 5/2012 | Kubo |
| 2012/0184938 | A1 | 7/2012 | Lev et al. |
| 2012/0215182 | A1 | 8/2012 | Mansour et al. |
| 2012/0220977 | A1 | 8/2012 | Yow |
| 2012/0220978 | A1 | 8/2012 | Lev et al. |
| 2012/0265163 | A1 | 10/2012 | Cheng et al. |
| 2012/0296307 | A1 | 11/2012 | Holt et al. |
| 2012/0310203 | A1 | 12/2012 | Khaled et al. |
| 2012/0323187 | A1 | 12/2012 | Iwase et al. |
| 2012/0323210 | A1 | 12/2012 | Lev et al. |
| 2013/0053814 | A1 | 2/2013 | Mueller-Beckhaus et al. |
| 2013/0096493 | A1 | 4/2013 | Kubo et al. |
| 2013/0144248 | A1 | 6/2013 | Putter et al. |
| 2013/0199669 | A1 | 8/2013 | Moy et al. |
| 2013/0231630 | A1 | 9/2013 | Kraus et al. |
| 2013/0237904 | A1 | 9/2013 | Deneburg et al. |
| 2013/0289530 | A1 | 10/2013 | Wyatt et al. |
| 2014/0020793 | A1 | 1/2014 | Denenburg et al. |
| 2014/0096862 | A1 | 4/2014 | Aneas |
| 2014/0150911 | A1 | 6/2014 | Hanner et al. |

FOREIGN PATENT DOCUMENTS

| | | | |
|---|---|---|---|
| DE | 4122476 | A1 | 1/1993 |
| DE | 202004012714 | U1 | 11/2004 |
| DE | 202009011019 | U1 | 12/2010 |
| EP | 0192661 | A1 | 9/1986 |
| EP | 0195018 | A1 | 9/1986 |
| EP | 0258913 | A2 | 3/1988 |
| EP | 0416454 | A2 | 3/1991 |
| EP | 0518397 | A1 | 12/1992 |
| EP | 0521460 | A1 | 1/1993 |
| EP | 0637443 | A1 | 2/1995 |
| EP | 19504413 | A1 | 8/1996 |
| EP | 0737467 | A1 | 10/1996 |
| EP | 761562 | A1 | 3/1997 |
| EP | 765652 | A1 | 4/1997 |
| EP | 765853 | A1 | 4/1997 |
| EP | 0806597 | A1 | 11/1997 |
| EP | 0814866 | A1 | 1/1998 |
| EP | 829248 | A2 | 3/1998 |
| EP | 0856331 | A2 | 8/1998 |
| EP | 882441 | A2 | 12/1998 |
| EP | 0887085 | A2 | 12/1998 |
| EP | 897708 | A2 | 2/1999 |
| EP | 0898951 | A2 | 3/1999 |
| EP | 960616 | A2 | 12/1999 |
| EP | 1008337 | A1 | 6/2000 |
| EP | 1029526 | A1 | 8/2000 |
| EP | 1034809 | A1 | 9/2000 |
| EP | 1051988 | A2 | 11/2000 |
| EP | 1323403 | A1 | 7/2003 |
| EP | 1329210 | A1 | 7/2003 |
| EP | 1396250 | A1 | 3/2004 |
| EP | 1454609 | A1 | 9/2004 |
| EP | 1454650 | A1 | 9/2004 |
| EP | 1498097 | A2 | 1/2005 |
| EP | 1872824 | A1 | 1/2008 |
| EP | 1911432 | A1 | 4/2008 |
| EP | 1919432 | A1 | 5/2008 |
| EP | 1930038 | A2 | 6/2008 |
| EP | 2090278 | A1 | 8/2009 |
| EP | 2351548 | A1 | 8/2011 |
| EP | 2351549 | A1 | 8/2011 |
| EP | 2462913 | A1 | 6/2012 |
| FR | 2029242 | A5 | 10/1970 |
| FR | 2856660 | A1 | 12/2004 |
| FR | 2869795 | A1 | 11/2005 |
| FR | 2931363 | A1 | 11/2009 |
| GB | 1444210 | A | 7/1976 |
| IL | 171662 | | 10/2005 |
| JP | 03-062426 | B | 9/1991 |
| JP | 4329954 | A | 11/1992 |
| JP | 06-050656 | U | 7/1994 |
| JP | H08-000710 | A | 1/1996 |
| JP | 09-104460 | A | 4/1997 |
| JP | 09-104461 | A | 4/1997 |
| JP | 10-118158 | A | 5/1998 |
| JP | H10-504736 | A | 5/1998 |
| JP | 11503627 | T | 3/1999 |
| JP | 11-319031 | A | 11/1999 |
| JP | 2000-508934 | A | 7/2000 |
| JP | 2000-237278 | A | 9/2000 |
| JP | 2001-505083 | A | 4/2001 |
| JP | 2002-035140 | A | 2/2002 |
| JP | 2002-516160 | A | 6/2002 |
| JP | 2002-355318 | A | 12/2002 |
| JP | 2003-033441 | A | 2/2003 |
| JP | 2003-102807 | A | 4/2003 |
| JP | 2004-097253 | A | 4/2004 |
| JP | 2004-522541 | A | 7/2004 |
| JP | 2010-179128 | A | 8/2010 |
| WO | 9003536 | A1 | 4/1990 |
| WO | 9403373 | A1 | 2/1994 |
| WO | 9507066 | A1 | 3/1995 |
| WO | 9600053 | A1 | 1/1996 |
| WO | 9629113 | A1 | 9/1996 |
| WO | 9736636 | A1 | 10/1997 |
| WO | 9832411 | A1 | 7/1998 |
| WO | 9837854 | A1 | 9/1998 |
| WO | 9961093 | A1 | 12/1999 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 0232372 | A1 | 4/2002 |
| WO | 0236191 | A2 | 5/2002 |
| WO | 02066100 | A2 | 8/2002 |
| WO | 02089900 | A1 | 11/2002 |
| WO | 03051423 | A2 | 6/2003 |

(56) References Cited

FOREIGN PATENT DOCUMENTS

| | | | | |
|---|---|---|---|---|
| WO | 03070147 | A2 | | 8/2003 |
| WO | 03079956 | A1 | | 10/2003 |
| WO | 2004041148 | A1 | | 5/2004 |
| WO | 2005002492 | A1 | | 1/2005 |
| WO | 2005041846 | A2 | | 5/2005 |
| WO | 2005105014 | A2 | | 11/2005 |
| WO | WO 2005105014 | A2 | * | 11/2005 |
| WO | WO 2006085327 | A1 | * | 8/2006 |
| WO | 2006099441 | A2 | | 9/2006 |
| WO | 2007015233 | A1 | | 2/2007 |
| WO | 2007017868 | A1 | | 2/2007 |
| WO | 2007052252 | A1 | | 5/2007 |
| WO | 2007101772 | A1 | | 9/2007 |
| WO | 2007105221 | A1 | | 9/2007 |
| WO | 2008081424 | A2 | | 7/2008 |
| WO | 2008126090 | A1 | | 10/2008 |
| WO | WO 2008126090 | A1 | * | 10/2008 |
| WO | 2009026443 | A2 | | 2/2009 |
| WO | 2009029010 | A1 | | 3/2009 |
| WO | 2009038860 | A2 | | 3/2009 |
| WO | 2009040804 | A2 | | 4/2009 |
| WO | 2009087572 | A1 | | 7/2009 |
| WO | 2009093249 | A1 | | 7/2009 |
| WO | 2009112489 | A1 | | 9/2009 |
| WO | 2009146088 | A1 | | 12/2009 |
| WO | 2010061743 | A1 | | 6/2010 |
| WO | 2010117580 | A1 | | 10/2010 |
| WO | 2011039747 | A1 | | 4/2011 |
| WO | 2011058545 | A1 | | 5/2011 |
| WO | 2011058548 | A1 | | 5/2011 |
| WO | 2011077434 | A1 | | 6/2011 |
| WO | 2011104711 | A1 | | 9/2011 |
| WO | 2012063230 | A1 | | 5/2012 |
| WO | 2012143921 | A1 | | 10/2012 |
| WO | 2013127813 | A1 | | 9/2013 |
| WO | 2013134246 | A1 | | 9/2013 |
| WO | 2013156944 | A1 | | 10/2013 |
| WO | 2014033706 | A2 | | 3/2014 |
| WO | 2014033710 | A1 | | 3/2014 |

OTHER PUBLICATIONS

Int'l Search Report and Written Opinion issued Sep. 2, 2014 in Int'l Application No. PCT/IL2014/050405.
Int'l Search Report and Written Opinion issued Oct. 17, 2014 in Int'l Application No. PCT/IL2014/050680.
English translation of an Office Action issued Aug. 28, 2014 in JP Application No. 2013-168885.
U.S. Appl. No. 29/478,723 by Lev, filed Jan. 8, 2014.
U.S. Appl. No. 29/478,726 by Lev, filed Jan. 8, 2014.
Office Action issued Jan. 2, 2014 in U.S. Appl. No. 13/505,881 by Lev.
Int'l Preliminary Report on Patentability issued Sep. 24, 2013 in Int'l Application No. PCT/IL2012/000354.
Office Action issued Feb. 13, 2014 in U.S. Appl. No. 13/884,981 by Denenburg.
U.S. Appl. No. 14/345,094 by Lev, filed Mar. 14, 2014.
Office Action issued May 6, 2014 in U.S. Appl. No. 13/505,881 by Lev.
U.S. Appl. No. 14/366,306 by Lev, filed Jun. 18, 2014.
Office Action issued Apr. 17, 2014 in CN Application No. 201080051201.4.
Int'l Search Report and Written Opinion issued Jul. 16, 2014 in Int'l Application No. PCT/IL2014/050327.
English translation of an Office Action issued Jun. 30, 2014 in CN Application No. 201180052962.6.
Extended European Search Report issued Jun. 3, 2014 in EP Application No. 08781828.2.
Written Opinion issued Jul. 1, 2013 in Int'l Application No. PCT/IL2013/050180.
Int'l Preliminary Report on Patentability issued Apr. 1, 2014 in Int'l Application No. PCT/IL2013/050180.
Written Opinion issued Jul. 31, 2013 in Int'l Application No. PCT/IL2013/050313.
Int'l Preliminary Report on Patentability issued May 12, 2014 in Int'l Application No. PCT/IL2013/050316.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/en/products/Pages/Mixject.aspx (admitted prior art).
http://www.westpharma.com/SiteCollectionDocuments/Recon/mixject%20product%20sheet.pdf; MIXJECT product information sheet pp. 1. (admitted prior art).
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued Jun. 19, 2006 in Int'l Application No. PCT/IL2005/000376.
Int'l Search Report Issued Aug. 25, 2008 in Int'l Application No. PCT/IL2008/000517.
Written Opinion of the ISR Issued Oct. 17, 2009 in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued Jan. 20, 2010 in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued on Mar. 17, 2011 in Int'l Application No. PCT/IL2010/000854.
Overview—Silicone Rubber [retrieved from http://www.knovel.com/web/portal/browse/display?_EXT_KNOVEL_DISPLAY_bookid=1023&VerticalID=0 on Feb. 9, 2011].

(56) References Cited

OTHER PUBLICATIONS

Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
Int'l Search Report issued Oct. 7, 2011 in Int'l Application No. PCT/IL2011/000511.
Int'l Search Report issued Mar. 6, 2012 in Int'l Application No. PCT/IL2011/000834; Written Opinion.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 2008801108283.4.
Written Opinion issued Jun. 5, 2013 in Int'l Application No. PCT/IL2012/050407.
Int'l Preliminary Report on Patentability issued Aug. 20, 2014 in Int'l Application No. PCT/IL2012/050407.
Office Action issued Jan. 2, 2015 in U.S. Appl. No. 29/438,141 by Gilboa.
Office Action issued Jan. 5, 2015 in U.S. Appl. No. 29/413,220 by Lev.
Office Action issued Jan. 7, 2015 in U.S. Appl. No. 29/438,134 by Lev.
Office Action issued Apr. 9, 2015 in U.S. Appl. No. 13/883,289 by Lev.
Office Action issued May 28, 2015 in U.S. Appl. No. 14/391,792 by Lev.
Office Action issued Mar. 6, 2012 in U.S. Appl. No. 12/678,928.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
Int'l Search Report issued Jun. 5, 2013 in Int'l Application No. PCT/IL2012/050407.
Int'l Search Report issued Jun. 19, 2013 in Int'l Application No. PCT/IL2013/050167.
Int'l Search Report issued Jul. 1, 2013 in Int'l Application No. PCT/IL2013/050180.
Int'l Search Report issued Jul. 31, 2013 in Int'l Application No. PCT/IL2013/050313.
Int'l Search Report issued Jul. 26, 2013 in Int'l Application No. PCT/IL2013/050316.
English translation of an Office Action issued Jun. 19, 2013 in JP Application No. 2012-531551.
Office Action issued Aug. 20, 2013 in U.S. Appl. No. 13/576,461 by Lev.
Int'l Preliminary Report on Patentability issued Aug. 28, 2012 in Int'l Application No. PCT/IL2011/000186.
English translation of an Office Action issued Jul. 26, 2013 in JP Application No. 2012-538464.
International Search Report Issued Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Drug Administration Systems product information sheets; http://www.westpharma.com/eu/en/products/Pages/Vial2Bag.aspx; pp. 1-3 (admitted prior art).
Office Action Issued Jun. 8, 2010 in U.S. Appl. No. 12/112,490 by Zinger.
Office Action issued Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007.html.> (7 pages. see pp. 5-6).
Office Action issued Jun. 15, 2011 in JP Application No. 2008-538492.
Translation of Office Action issued Jun. 18, 2012 in JP Application No. 2008-538492.
Translation of Office Action issued Apr. 15, 2013 in JP Application No. 2008-538492.
Office Action issued Jul. 13, 2012 in U.S. Appl. No. 12/112,490 by Zinger.
Office Action issued Jan. 23, 2013 in U.S. Appl. No. 12/112,490 by Zinger.
Int'l Preliminary Report on Patentability issued May 6, 2008 in Int'l Application No. PCT/IL2006/001228.
Written Opinion issued Aug. 16, 2012 in Int'l Application No. PCT/IL2012/000164.
English translation of an Office Action issued Sep. 10, 2013 in JP Application No. 2012-554468.
Office Action issued Nov. 11, 2013 in IL Application No. 218730.
Int'l Search Report and Written Opinion issued Jan. 7, 2014 in Int'l Application No. PCT/IL2012/050721.
English translation of an Office Action issued Jan. 9, 2014 in JP Application No. 2010-526421.
English translation of an Office Action issued Dec. 4, 2013 in CN Application No. 201080051210.3.
English translation of an Office Action issued Dec. 25, 2013 in CN Application No. 201180006530.1.
Office Action issued Nov. 28, 2013 in IN Application No. 4348/DELNP/2008.
Office Action issued Oct. 8, 2013 in CN Application No. 201080043825.1.
English translation of an Office Action issued Feb. 4, 2014 in JP Application No. 2012-554468.
Office Action issued Jan. 17, 2014 in CN Application No. 201180006534.X.
Int'l Search Report and Written Opinion issued May 8, 2014 in Int'l Application No. PCT/IL2013/050706.
English translation of an Office Action issued Apr. 28, 2014 in JP Application No. 2013-537257.
Int'l Preliminary Report on Patentability issued Jan. 14, 2014 in Int'l Application No. PCT/IL2012/050516.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
Alaris Medical Systems Product Brochure, 4 pages, Issue 1, Oct. 11, 1999.
Smart Site Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Int'l Search Report issued Aug. 16, 2012 in Int'l Application No. PCT/IL2012/000164.
U.S. Appl. No. 29/438,134 by Lev, filed Nov. 27, 2012.
U.S. Appl. No. 29/438,141 by Gilboa, filed Nov. 27, 2012.
Int'l Search Report issued Jan. 22, 2013 in Int'l Application No. PCT/IL2012/000354.
Int'l Search Report issued Mar. 18, 2013 in Int'l Application No. PCT/IL2012/050516.
Office Action issued Apr. 2, 2013 in U.S. Appl. No. 13/505,790.

(56) References Cited

OTHER PUBLICATIONS

Int'l Search Report and Written Opinion issued Mar. 6, 2012 in Int'l Application No. PCT/IL2011/000834.
U.S. Appl. No. 13/883,289 by Lev, filed May 3, 2013.
Int'l Search Report & Written Opinion issued on Mar. 7, 2012 in Int'l Application No. PCT/IL2011/000829.
U.S. Appl. No. 13/884,981 by Denenburg, filed May 13, 2013.
Office Action issued May 31, 2013 in U.S. Appl. No. 13/505,790.

* cited by examiner

INLINE LIQUID DRUG MEDICAL DEVICES WITH LINEAR DISPLACEABLE SLIDING FLOW CONTROL MEMBER

CROSS-REFERENCE TO RELATED APPLICATION

This application is a continuation of co-pending U.S. application Ser. No. 13/505,881, filed May 3, 2012, entitled "Inline Liquid Drug Medical Devices with Linear Displaceable Sliding Flow Control Member", which is a Section 371 of International Application No. PCT/IL2010/000915, filed Nov. 4, 2010, which was published in the English language on May 19, 2011, under International Publication No. WO 2011/058548 A1, and the disclosure of each of which is incorporated herein by reference.

FIELD OF THE INVENTION

The invention relates to inline liquid drug medical devices for liquid drug reconstitution and administration purposes.

BACKGROUND OF THE INVENTION

Commonly owned U.S. Pat. No. 6,238,372 entitled Fluid Control Device illustrates and describes a fluid control device for use with a syringe and at least one medicinal vessel. The fluid control device includes a first port, a second port for receiving the syringe, a third port including an adaptor having a fluid conduit member extending into the interior of the medicinal vessel when attached thereto and a flow control member selectively disposable from a first flow control position enabling a flow path between a first pair of two ports and second flow control position enabling a flow path between a second pair of two ports. The flow control member is coupled to one of the ports for manipulation between its flow control positions.

Commonly owned PCT International Application No. PCT/IL2005/000376 entitled Liquid Drug Medical Devices and published under PCT International Publication No. WO 2005/105014 illustrates and describes a liquid drug medical device for liquid drug reconstitution and administration purposes, a vial adapter with elastomer tubing and a needle shield removal device. The liquid drug medical device has a longitudinal axis and is intended for use with a source of physiological solution and a medicinal vessel. The liquid drug medical device includes a body member having a first port for fluid connection with the source of physiological solution and a flow control member rotatably mounted in the body member about an axis of rotation co-directional with the longitudinal axis. The flow control member has a first major flow duct and a second major flow duct substantially parallel to and non-coaxial with the axis of rotation and respectively terminating at a second port, and a third port for administering the liquid drug. The liquid drug medical device further includes a manually rotatable adapter having a fluid conduit member with a proximal end in flow communication with the second port and a distal end extending into the medicinal vessel on its attachment to the adapter, and coupled to the flow control member for rotating same between a first flow control position for connecting the first port with the second port, and a second flow control position for connecting the first port with the third port.

Commonly owned PCT International Application No. PCT/US2008/070024 entitled Medicament Mixing and Injection Apparatus and published under PCT International Publication No. WO 2009/038860 illustrates and describes a mixing and injection apparatus including a needle and a needle base, a syringe attachment element and a mixing chamber engagement assembly including a needle chamber surrounding the needle and a first liquid conduit portion, sealed from the needle chamber and a mixing chamber engagement portion including a second liquid conduit portion communicating with the first liquid conduit portion and configured for communication with a mixing chamber. The syringe attachment element and the needle base are configured to permit liquid communication between an interior of the syringe and the first liquid conduit portion when the syringe attachment element and the needle base are in the first relative engagement orientation and to permit liquid communication between an interior of the syringe and the needle when the syringe attachment element and the needle base are in the second relative engagement orientation, axially separated from the first relative orientation along the injection axis.

BRIEF SUMMARY OF THE INVENTION

The present invention is directed toward inline liquid drug medical devices for use with a source of physiological fluid and a medicinal vessel for liquid drug reconstitution and administration purposes.

The inline liquid drug medical device includes a housing having a longitudinal device axis and a vial adapter removably attached on the housing and detachable therefrom along a line of detachment co-directional with the device axis. The housing has three ports, a first port onto which is connected the source of physiological fluid, a second port which leads to the medicinal vessel, and a third port which is fitted with a drug dispenser such as a needle, an atomizer, and the like.

The inline liquid drug medical device includes a manually operated actuating mechanism for applying a linear displacement force to a flow control member sealingly accommodated inside a bore in the housing for sliding the flow control member along the bore in a transverse direction to the device axis from an initial first flow control position for liquid drug reconstitution purposes to a subsequent second flow control position for liquid drug administration purposes. The first flow control position enables flow communication between the first port and the second port for liquid drug reconstitution purposes. The second flow control position enables flow communication between the first port and the third port fitted with a drug dispenser such as a needle, an atomizer, and the like, for liquid drug administration purposes. The first and third ports are preferably co-axial for facilitating more intuitive use of the device.

The actuating mechanism has an initial liquid drug reconstitution position corresponding with the flow control member's first flow control position and a subsequent liquid drug administration position corresponding with the flow control member's second flow control position. One type of actuating mechanism employs a manual radial actuation force having a component for imparting a linear displacement force to the flow control member. Another type of actuating mechanism employs a manual linear actuation force for imparting a linear displacement force to a flow control member. Actuating mechanisms are preferably integrally formed with vial adapters for removal together with the vial adapters on detaching same from a housing after liquid drug reconstitution and prior to liquid drug administration. Alternatively, the actuating mechanisms can be integrally formed with the housings.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DESCRIPTION OF THE DISCLOSURE

Figure 1:
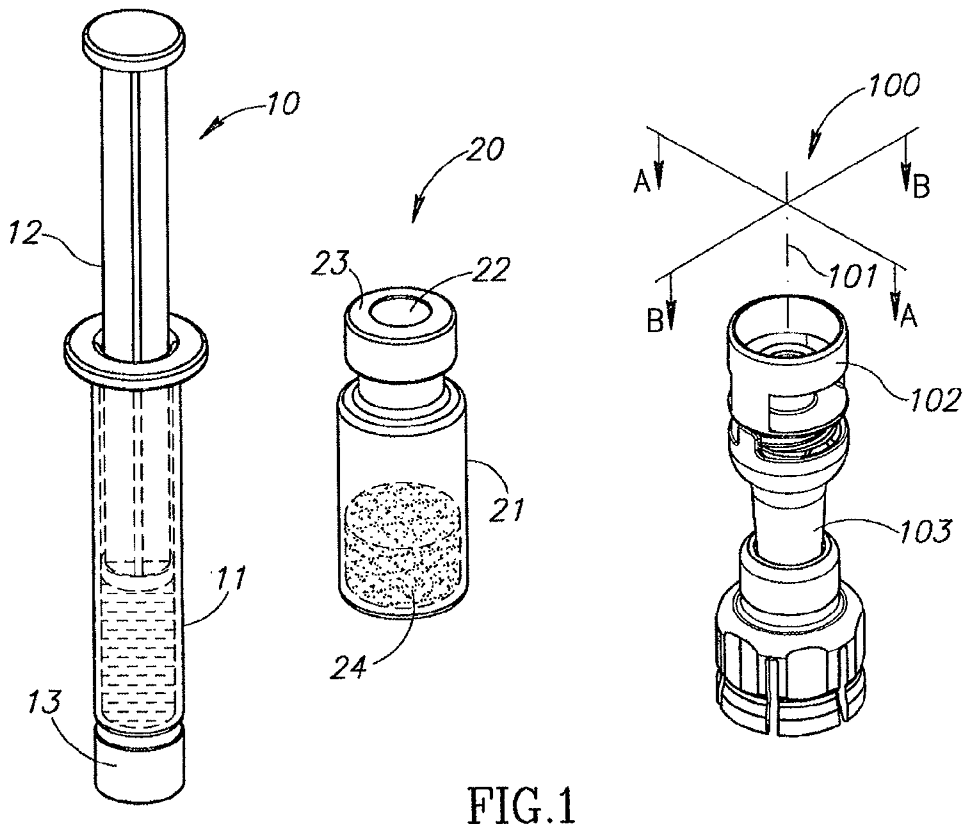
FIG. 1 is a pictorial representation of a syringe, a vial and an inline liquid drug medical device having a rotary actuating mechanism and a linear displaceable sliding flow control member.
Figure 2:
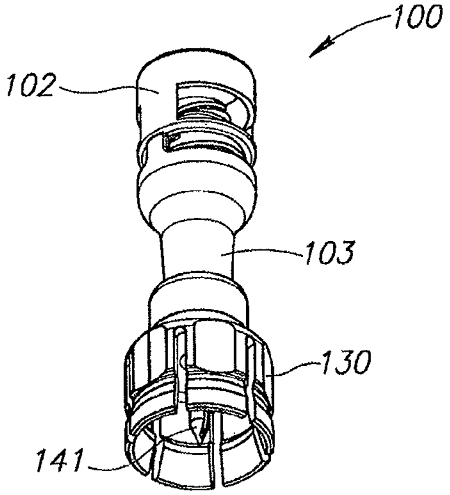
FIG. 2 is a bottom perspective view of FIG. 1's device.

Inline Liquid Drug Medical Device including a Manually Operated Rotary Actuating Mechanism and a Linear Displaceable Sliding Flow Control Member FIG. 1 shows a syringe 10 constituting a source of physiological fluid, a vial 20 constituting a medicinal vessel and an inline liquid drug medical device 100 for use with the syringe 10 and the vial 20. The syringe 10 includes a barrel 11 with a plunger 12 and a male Luer lock connector 13. The syringe 10 can be formed with other types of connectors. The vial 20 includes an open topped bottle 21 sealed by a vial stopper 22 capped by a metal band 23 or other suitable capping material. The vial 20 contains either a powdered or liquid drug 24. The syringe 10 typically contains diluent for reconstituting the vial contents 24.

FIGS. 2 to 6 show the inline liquid drug medical device 100 having a longitudinal device axis 101 and including a housing 102 and a vial adapter 103 removably coupled on the housing 102 and detachable therefrom along a line of detachment co-directional with the device axis 101. The housing 102 includes a generally cylindrical body 104 coaxial with the device axis 101 and having a syringe port 108 at one end and a port manifold 109 at its opposing end. The body 104 includes a throughgoing bore 106 having a bore axis 107 transversely directed to the device axis 101, a proximal bore end 106A and a distal bore end 106B. The body 104 includes a threaded intermediate section 112 with circumferentially surrounding fastening threads 112A. An annular hand held sleeve 111 coaxially aligned with the device axis 101 is attached to the intermediate section 112 by two opposite attachment walls 118 for enabling a user to conformably grip the housing 102 during use. The sleeve 111 includes a sleeve opening 111A for allowing access to the syringe port 108.

The syringe port 108 constitutes a first port in flow communication with the bore 106. The syringe port 108 is intended to the syringe's connector 13 and is co-directional with the device axis 101 and preferably co-axial therewith. The syringe port 108 is typically in the form of a female Luer connector intended for receiving a syringe's male Luer lock connector. The port manifold 109 is generally cylindrically shaped and is coaxially aligned with the device axis 101. The port manifold 109 includes a second port 113 and a third port 114 both in flow communication with the bore 106. The second port 113 and the third port 114 are co-directional with the device axis 101 and the third port 114 is preferably coaxial therewith. The third port 114 is preferably fitted with a needle 116 for liquid drug administration purposes. The second port 113 is preferably recessed with respect to the third port 114 thereby forming an annular cavity 117 for removably coupling the vial adapter 103 on the housing 102.

The device 100 includes a linear displaceable sliding flow control member (FCM) 120 sealingly accommodated in the bore 106 for establishing flow communication between the syringe port 108 and the second port 113 in a first flow control position for liquid drug reconstitution purposes, and between the syringe port 108 and the third port 114 in a second flow control position for liquid drug administration purposes. The flow control member 120 is of a generally cylindrical shape and has a peripheral cylindrical surface 121 with a semi-circular peripheral flow channel 122 and a longitudinally directed flow cutout 123, a blind bore 124, a proximal FCM end 126, and a distal FCM end 127.

A proximal rounded protrusion 128 extends beyond the proximal FCM end 126, and serves as an abutment surface for applying a radial actuation force RAF thereagainst to impart a linear displacement force LDF to urge the flow control member 120 along the bore 106. In the first flow control position, the flow control member 120 is sealingly inserted in the bore 106 with the proximal rounded protrusion 128 substantially protruding out of the proximal bore end 106A (see FIGS. 5A-5D). In the second flow control position, the proximal rounded protrusion 128 is substantially wholly inserted in the proximal bore end 106A (see FIGS. 6A-6C).

The longitudinally directed flow cutout 123 is dimensioned so that it is in flow communication with the first port 108 when the flow control member 120 is in both its first flow control position and its second flow control position. The flow channel 122 is disposed towards the proximal FCM end 126 circumferentially extends from a proximal channel end 122A in flow communication with the flow cutout 123 to a distal channel end 122B. In the first flow control position, the distal channel end 122B is in flow communication with the second port 113 (see FIG. 5A), and in the second flow control position, the distal channel end 122B is in flow communication with the third port 114 (see FIG. 6A).

The vial adapter 103 includes a skirt 130 with a top surface 131 and downward depending flex members 132 for snap fitting onto the vial 20. The vial adapter 103 includes an elongated upright stem 133 and terminating in a circular stem end portion 134 having a stem cavity 135 shaped for accommodating onto the housing 102. The stem cavity 135 includes an upper body cavity section 135A for rotatably fitting onto the generally cylindrical body 104 and a cylindrically shaped lower manifold cavity section 135B for rotatably fitting onto the port manifold 109.

The stem 133 includes an annular manifold support 136 at a distal end of the lower manifold cavity section 135B for circumferentially coupling with the annular cavity 117. A fluid conduit 137 which is co-axial with the device axis 101 has a proximal end 137A in the annular manifold support 136 for sealed flow communication with the second port 113 on coupling the vial adapter 103 to the housing 102. The fluid conduit 137 fluidly connects at a distal end 137B to a co-axial puncturing cannula 141 through a fluid interconnect conduit 137C. The puncturing cannula 141 serves to puncture the vial stopper 22 on its positive insertion into the vial adapter 103, and extends slightly therebeyond so that on inverting the vial 20 its nearly entire contents 24 can be aspirated therefrom through the puncturing cannula 141 to syringe 10. The stem 133 also includes a blind needle bore 138 for receiving the needle 116 on coupling the vial adapter 103 on the housing 102.

Figure 3A:
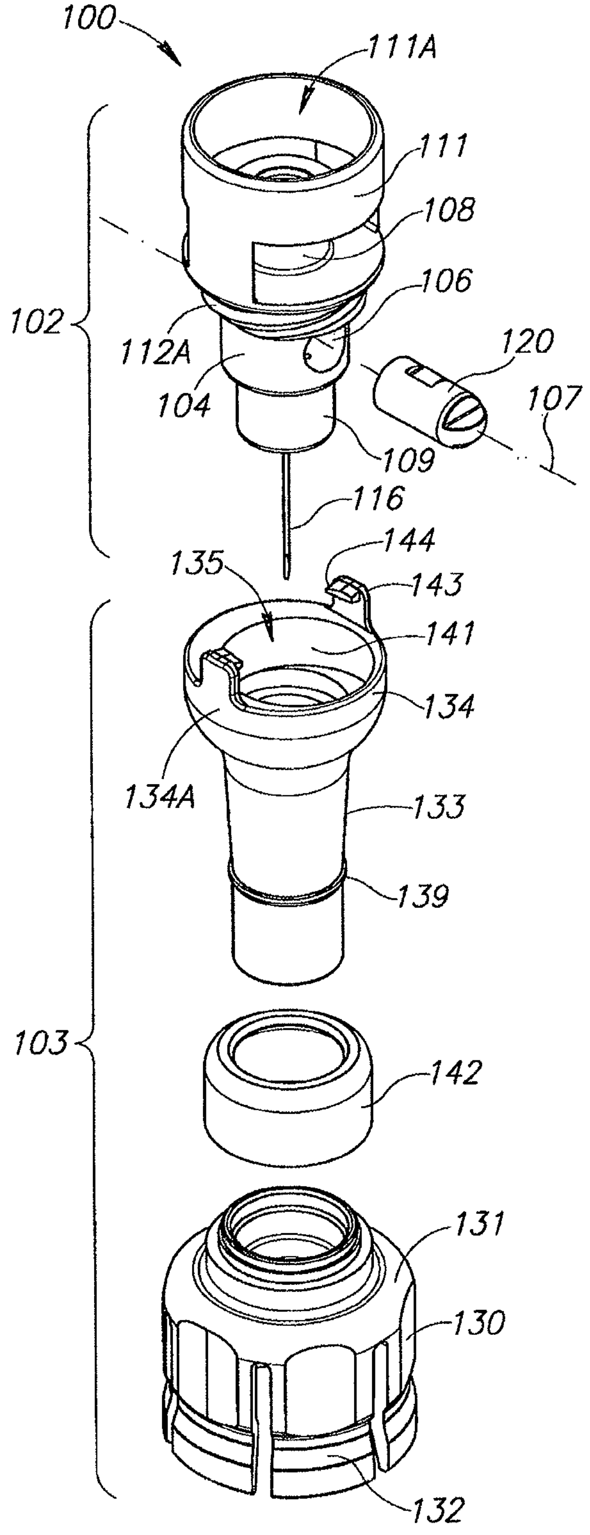
FIG. 3A is a partially exploded view of FIG. 1's device.
Figure 3B:
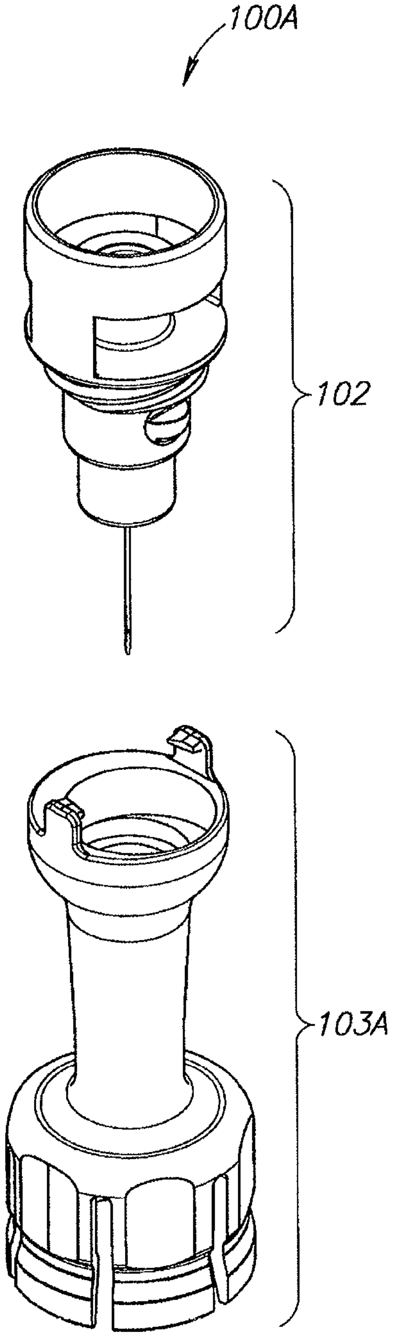
FIG. 3B is a partially exploded view of another embodiment of FIG. 1's device with an integral vial adapter.
Figure 4A:
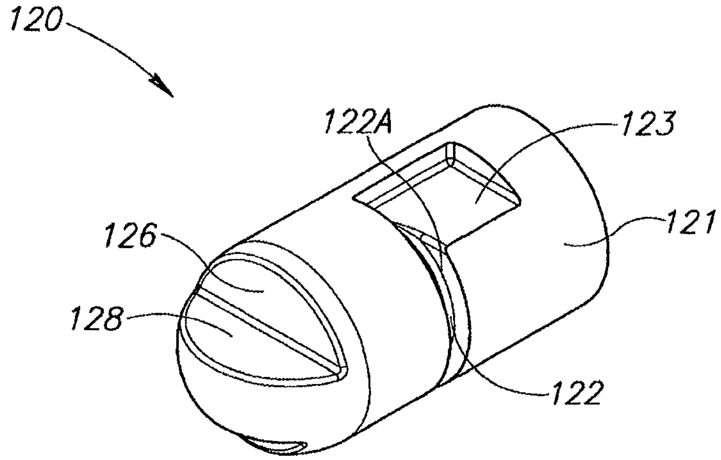
FIG. 4A is a top perspective view of FIG. 1's device's flow control member.
Figure 4B:
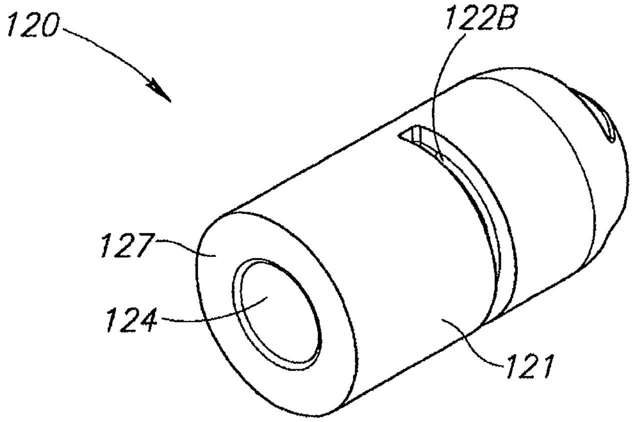
FIG. 4B is a bottom perspective view of FIG. 1's device's flow control member.
Figure 5A:
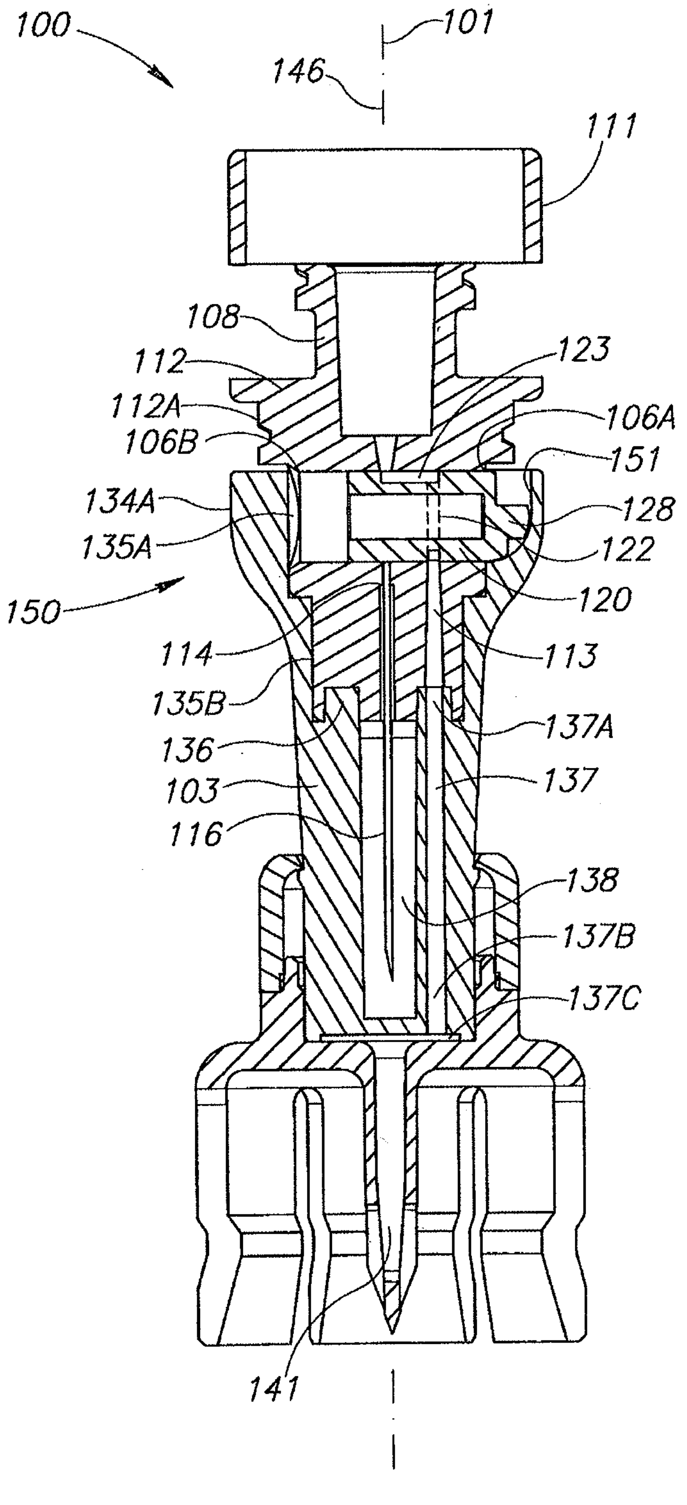
FIGS. 5A and 5B are longitudinal cross sections of FIG. 1's device along lines A-A and B-B, respectively, in FIG. 1 showing its actuating mechanism in an initial liquid drug reconstitution position and its flow control member in a first flow control position for liquid drug reconstitution purposes.
Figure 5B:
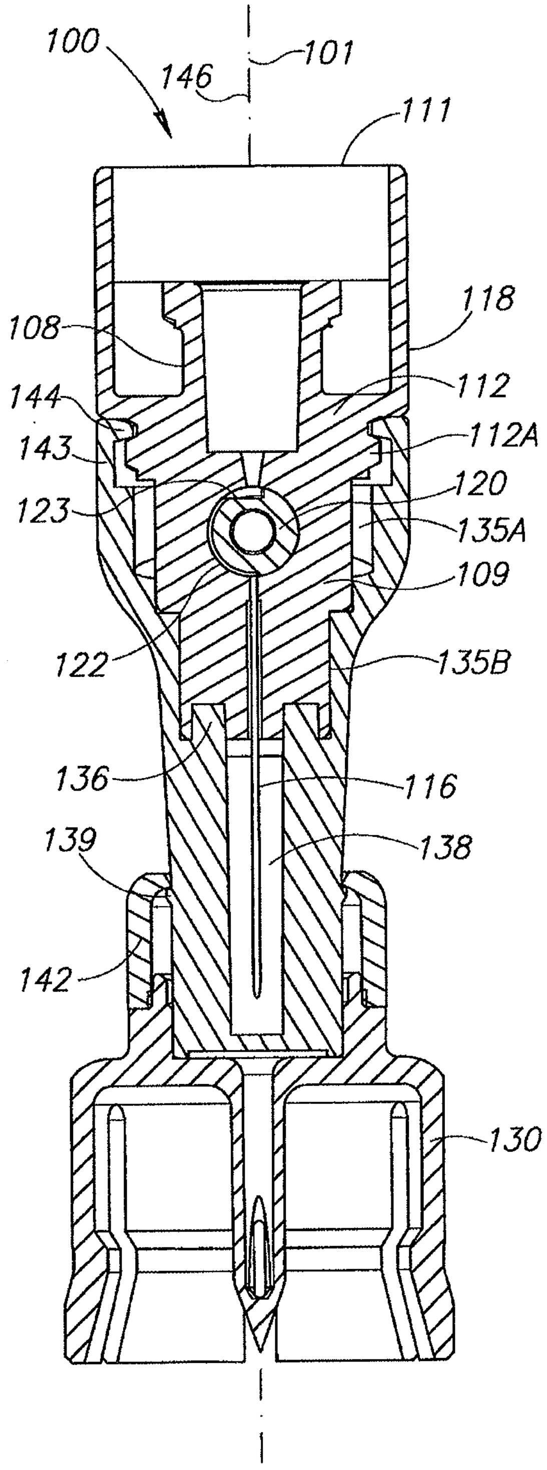
Figure 5C:
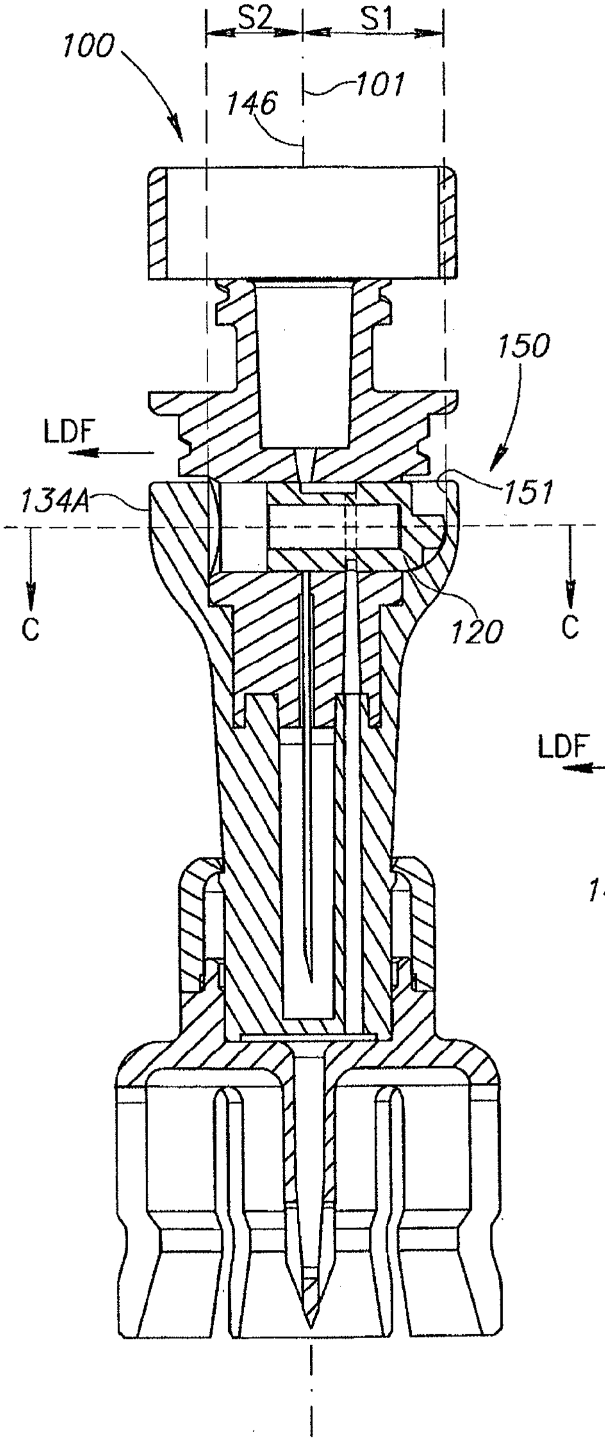
FIG. 5C is similar to FIG. 5A showing the separation distances S1 and S2 between opposite internal surfaces of the actuating mechanism relative to its axis of rotation.
Figure 5D:
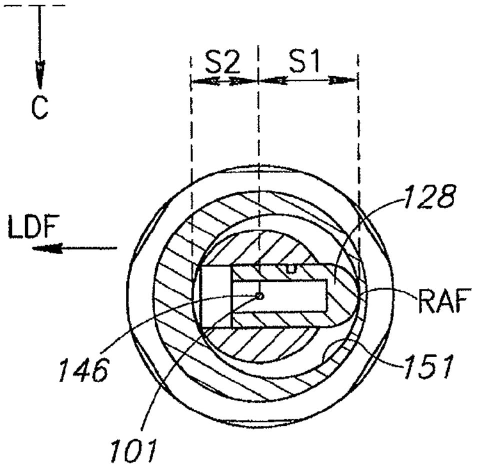
FIG. 5D is a transverse cross section of FIG. 1's device along line C-C in FIG. 5C showing the separation distances S1 and S2 between opposite internal surfaces of the actuating mechanism relative to its axis of rotation.

In a first embodiment, as shown in FIG. 3A, the stem 133 has a circumferential rim 139 along a bottom section for engaging a coupler 142 which secures the stem 133 to the top surface 131. In another embodiment, as shown in FIG. 3B, a device 100A similar to device 100 includes an integrally built vial adapter 103A which is removably coupled to the housing 102.

The vial adapter 103 is screw threaded onto the housing 102 by means of a pair of opposite fastening members 143 extending upright from the stem end portion 134 co-directional and on opposing sides of the device axis 101. The fastening members 143 each have a perpendicularly projecting tooth 144 for engaging the fastening threads 112A. As the vial adapter 103 is rotated relative to the housing 102 about an axis of rotation 146 co-axial with the device axis 101, the vial adapter 103 unscrews from the housing 102 and is detachable therefrom along a line of detachment co-directional with the device axis 101.

The vial adapter 103 is integrally formed with a manually operated rotary actuating mechanism 150 for applying a radial actuation force RAF for imparting a linear displacement force LDF for sliding the flow control member 120 along the bore 106 from its first flow control position to its second flow control position. The actuating mechanism 150 is implemented by employing a semi-circular internal cam surface 151 of the stem end portion 134 for bearing against the proximal rounded protrusion 128 as the vial adapter 103 is rotationally detached from the housing 102. The actuating mechanism 150 has an initial liquid drug reconstitution position corresponding to the flow control member 120's first flow control position when the vial adapter 103 is screw threaded attached on the housing 102 and a subsequent liquid drug administration position corresponding with the flow control member 120's second flow control position when the vial adapter 103 is detachable from the housing 102. The internal cam surface 151 defines a separation (S) relative to the axis of rotation 146. The internal cam surface 151 has a maximum separation S1 at the actuating mechanism 150's liquid drug reconstitution position and a minimum separation S2 in actuating mechanism 150's liquid drug administration position. The separation S2 is smaller than the separation S1 such that as the vial adapter 103 is screw unthreaded from the housing 102, the internal cam surface 151 applies a radial actuation force RAF against the protrusion 128 having a component for imparting a linear displacement force (LDF) to the flow control member 120 for sliding same along the bore 106 from its first flow control position to its second flow control position. The stem end portion 134 has an external surface 134A with a uniform radius relative to the axis of rotation 146 such that its wall thickness increases from its thinnest where the internal cam surface 151 abuts the flow control member 120 at the actuating mechanism's liquid drug reconstitution position to its thickest where the internal cam surface 151 abuts the flow control member 120 at the actuating mechanism's liquid drug administration position.

Operation of the device 100 may best be explained by referring to FIGS. 5A-5D and FIGS. 6A-6C.

FIGS. 5A-5D show the actuating mechanism 150 in its initial liquid drug reconstitution position and the flow control member 120 in its first flow control position. The vial adapter 103 is screw threaded onto the housing 102 and the flow control member 120 protrudes from the proximal bore end 106A with the proximal rounded protrusion 128 abutting the internal cam surface 151.

Figure 6A:
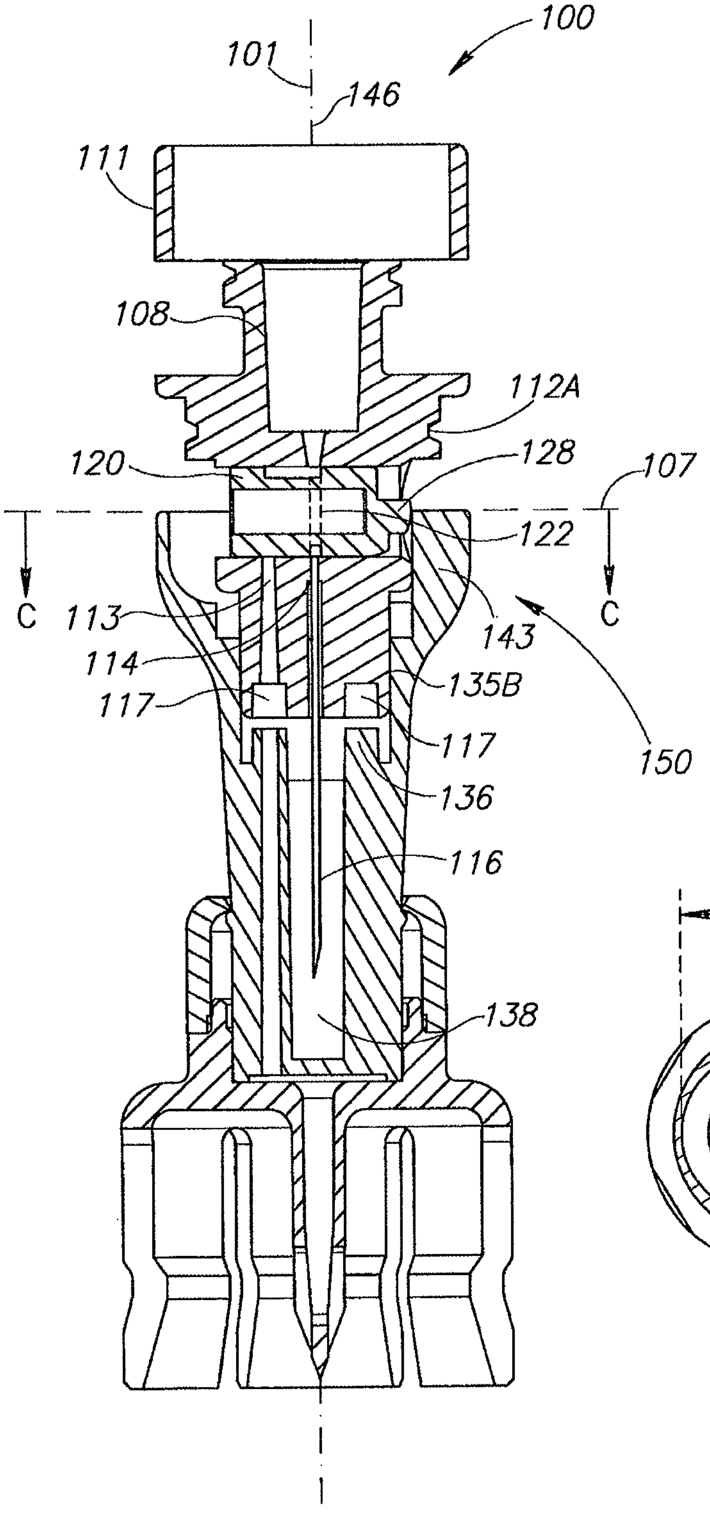
FIG. 6A is a longitudinal cross section of FIG. 1's device along line A-A in FIG. 1 showing its actuating mechanism in a subsequent liquid drug administration position and its flow control member in a second flow control position for liquid drug administration purposes.
Figure 6B:
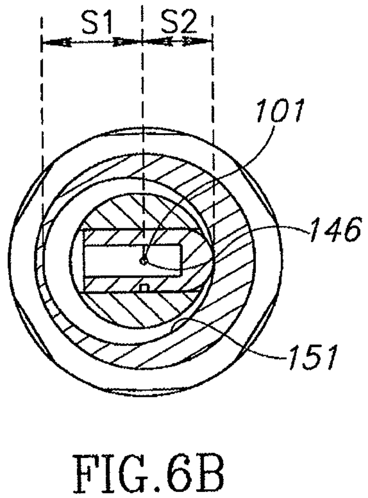
FIG. 6B is a transverse cross section of FIG. 1's device along line C-C in FIG. 6A showing its actuating mechanism in its subsequent liquid drug administration position and its flow control member in its second flow control position for liquid drug administration purposes.
Figure 6C:
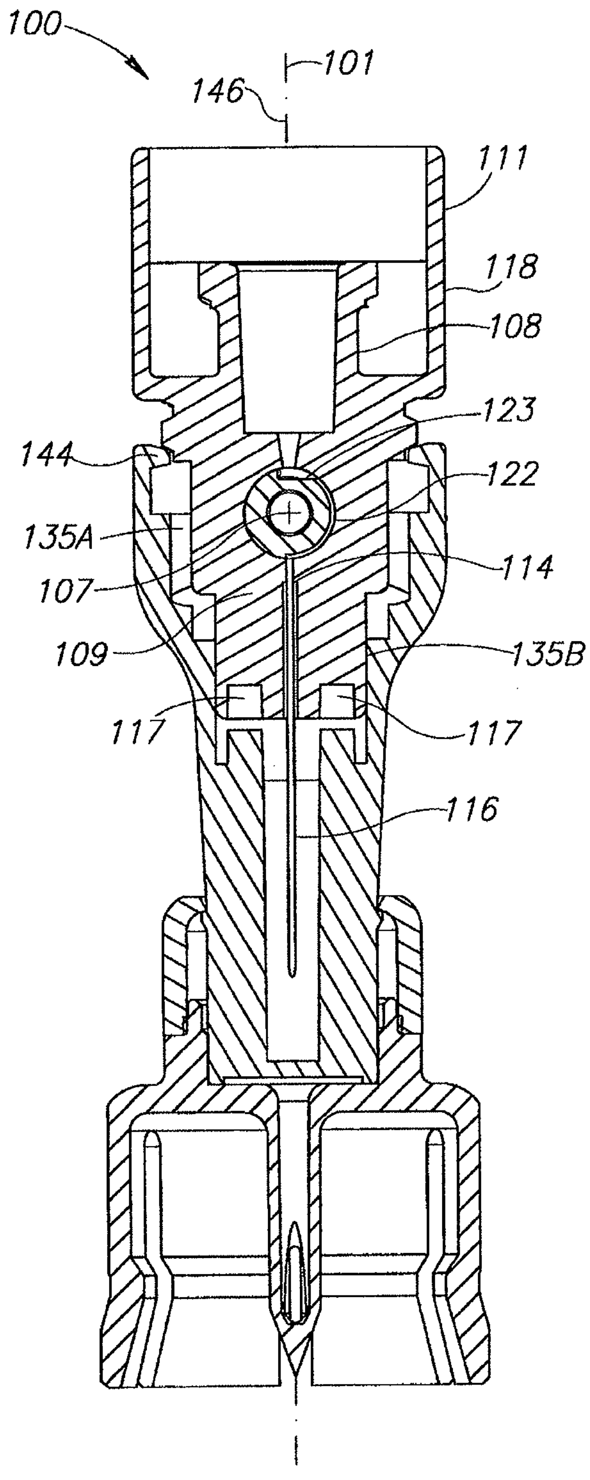
FIG. 6C is a longitudinal cross section of FIG. 1's device along line B-B in FIG. 1 showing its actuating mechanism in its liquid drug administration position and its flow control member in its second flow control position for liquid drug administration purposes.

FIGS. 6A-6C show the actuating mechanism 150 in its subsequent liquid drug administration position and the flow control member 120 in its second flow control position after a half turn unthreading the vial adapter 103 from the housing 102. The radial actuation force RAF is continuously applied to the flow control member 120 by the internal cam surface 151 having a continuously decreasing separation S from the axis of rotation 146 for imparting the linear displacement force LDF to slidingly displace the flow control member 120 to its second flow control position. The teeth 144 fully disengage from the fastening threads 112A at the actuating mechanism's liquid drug administration position when the flow control member 120 is in the second flow control position at which time the vial adapter 103 is detachable from the housing 102.

Figure 7D:
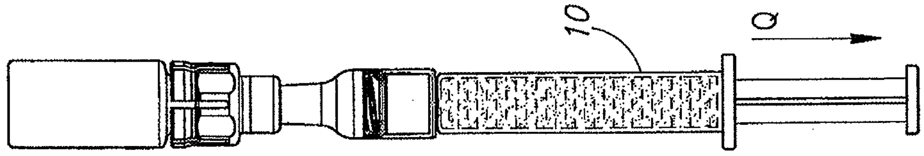
FIGS. 7A to 7G show the use of FIG. 1's device for liquid drug reconstitution and administration purposes.
Figure 7C:
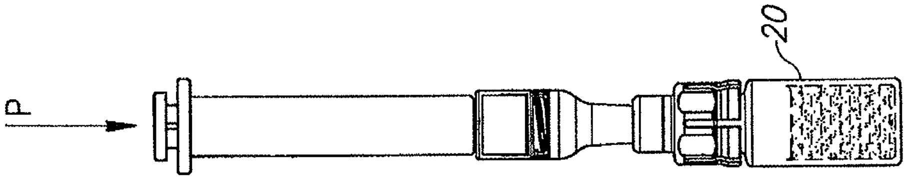
Figure 7B:
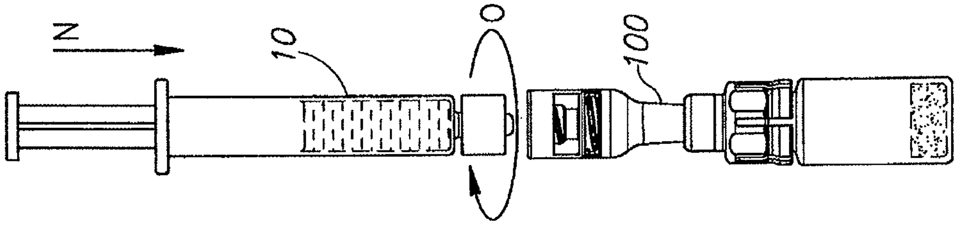
Figure 7A:
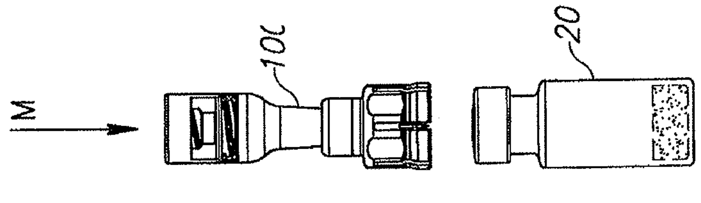

The use of the inline liquid drug medical device 100 for liquid drug reconstitution and administration is shown in FIGS. 7A to 7G as follows:

FIG. 7A shows the device 100 is in its initial first flow control position for liquid drug reconstitution and a user mounting the device 100 on a vial 20, as indicated by arrow M.

FIG. 7B shows the user approximating the syringe 10 towards the device 100, as indicated by arrow N, and screw threading the syringe 10 onto the device 100, as indicated by arrow O.

FIG. 7C shows the user injecting the syringe's contents into the vial 20, as indicated by arrow P. The user agitates the assemblage for reconstituting the liquid drug.

FIG. 7D shows the user inverting the assemblage and aspirating the reconstituted liquid drug contents into the syringe 10, as indicated by arrow Q.

Figure 7G:
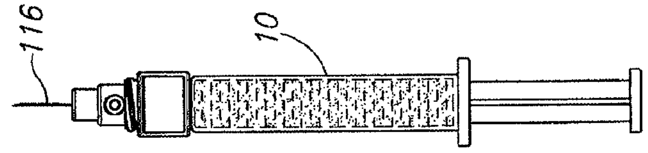
Figure 7F:
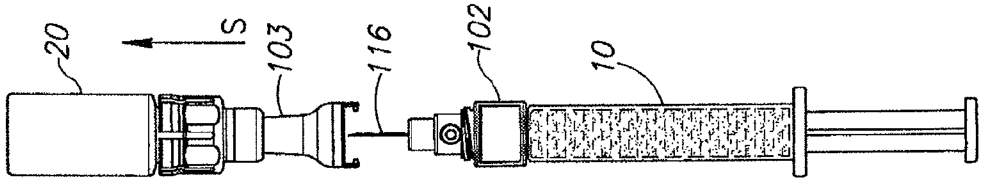
Figure 7E:
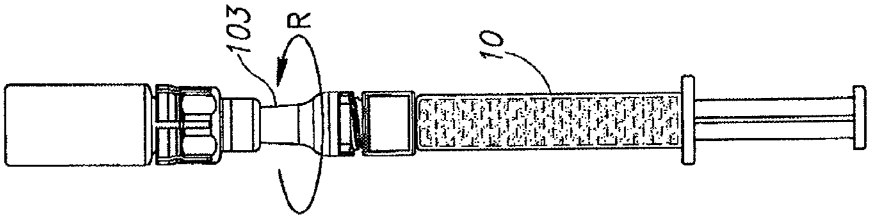

FIG. 7E shows the user rotating the vial adapter 103 to the subsequent liquid drug administration position for slidingly displacing the flow control member 120 to its subsequent second flow control position, as indicated by arrow R. Optionally, for this step and the following steps, the user inverts the assemblage so that the syringe 10 is above the vial 20.

FIG. 7F shows the user screw threading the vial adapter 103 from the housing 102, as indicated by arrow S for exposing the needle 116, thereby enabling administration of the liquid drug (see FIG. 7G). The user disposes of the vial adapter 103 with the spent vial 20.

Figure 8:
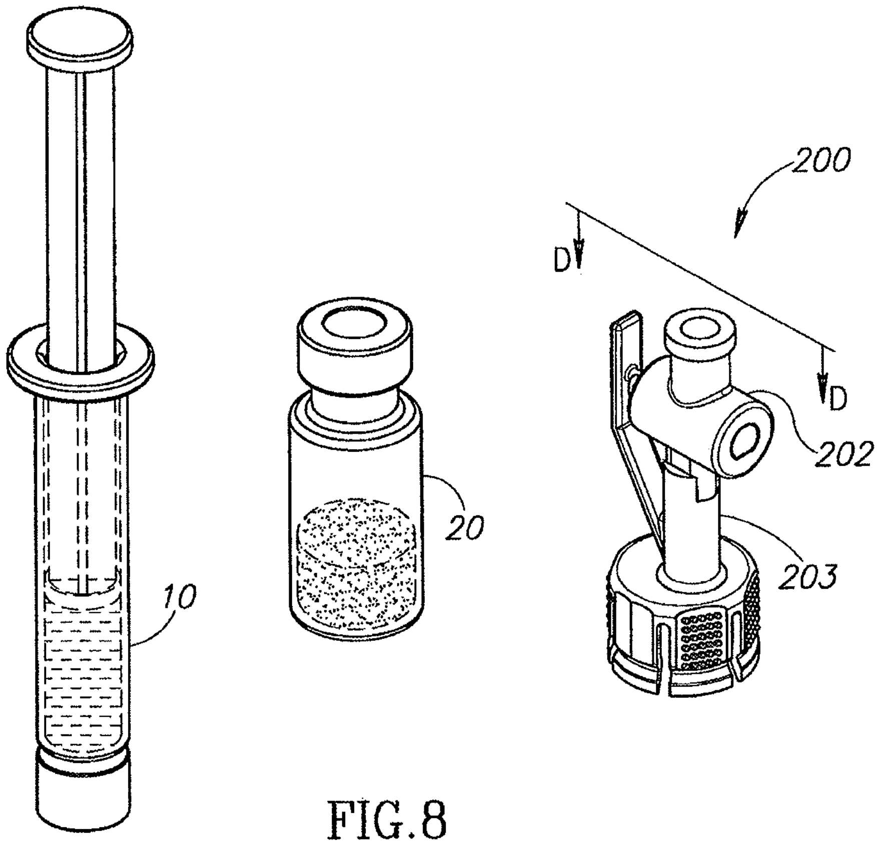
FIG. 8 is a pictorial representation of a syringe, a vial and an inline liquid drug medical device having an actuating mechanism with a spring leaf like actuator, and a linear displaceable sliding flow control member.
Figure 9:
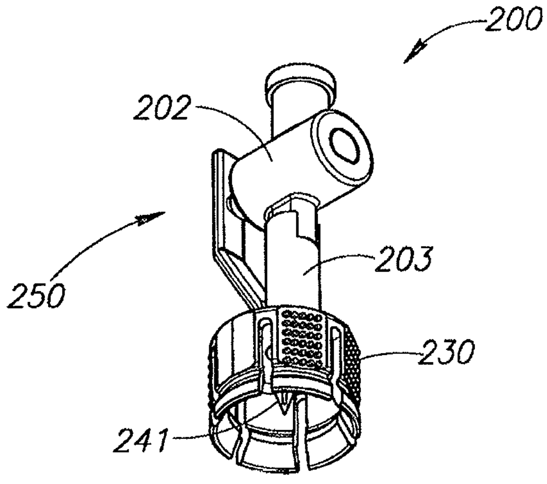
FIG. 9 is a bottom perspective view of FIG. 8's device.
Figure 10:
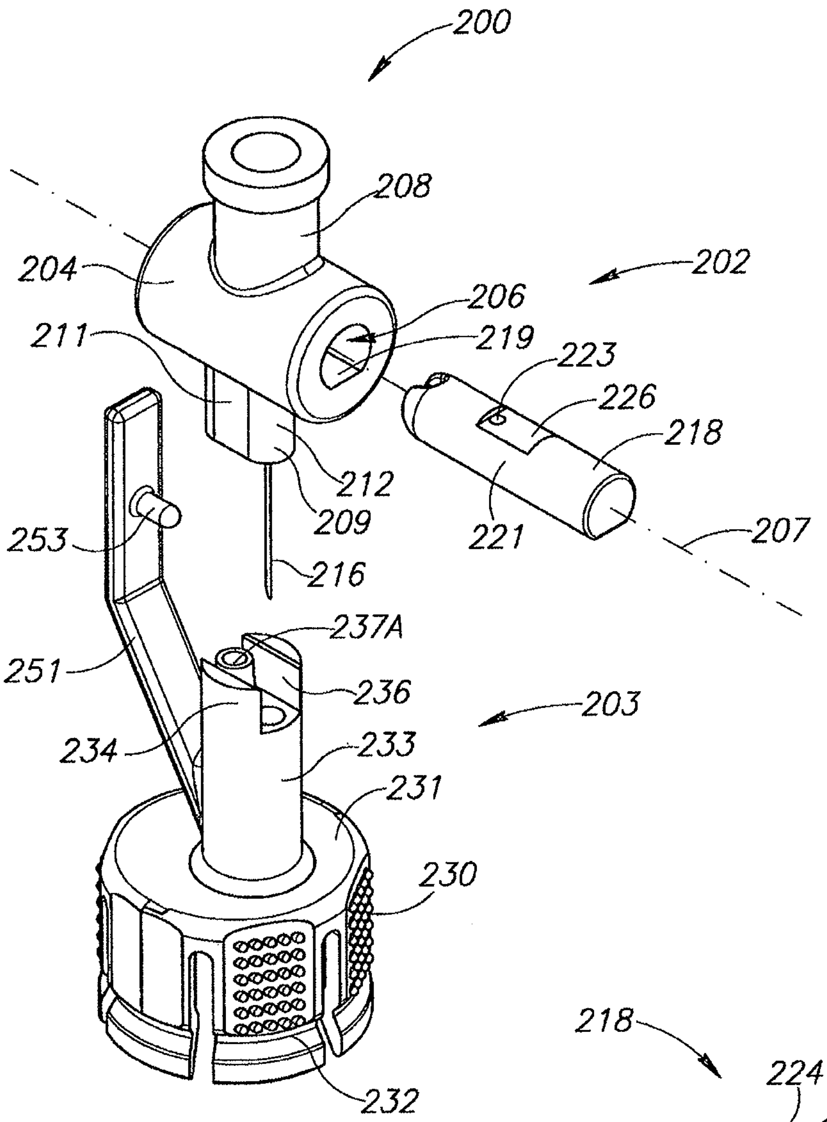
FIG. 10 is a partially exploded view of FIG. 8's device.
Figure 11:
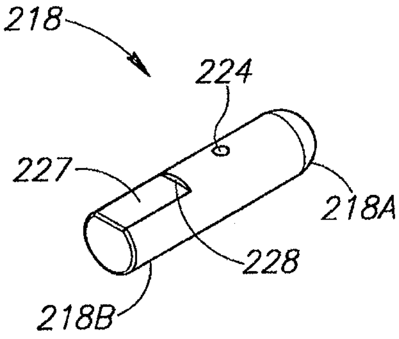
FIG. 11 is a top perspective view of FIG. 8's device's flow control member.
Figure 12:
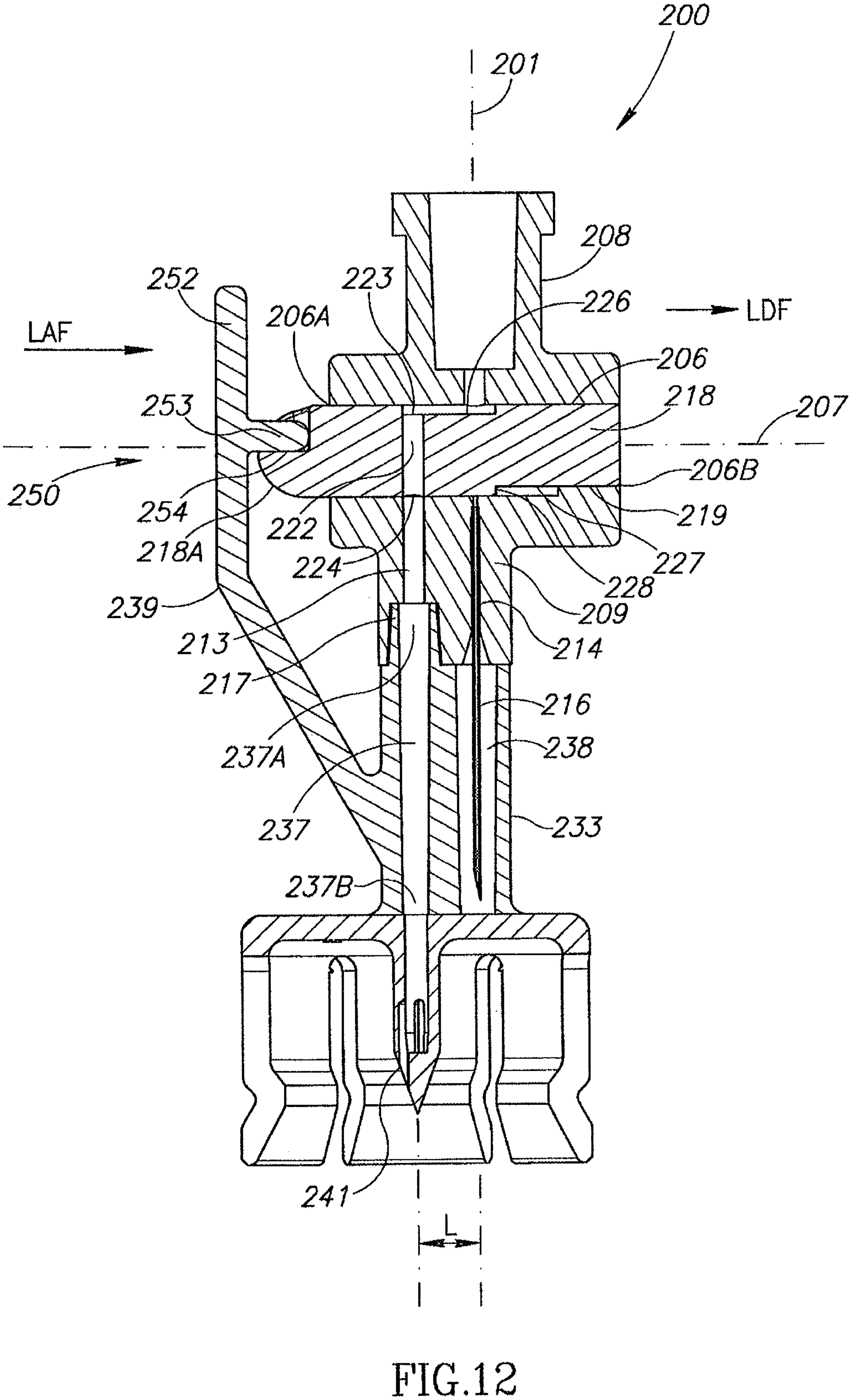
FIG. 12 is a longitudinal cross section of FIG. 8's device along line D-D in FIG. 8 showing its actuating mechanism in an initial liquid drug reconstitution position and its flow control member in a first flow control position for liquid drug reconstitution purposes.
Figure 13:
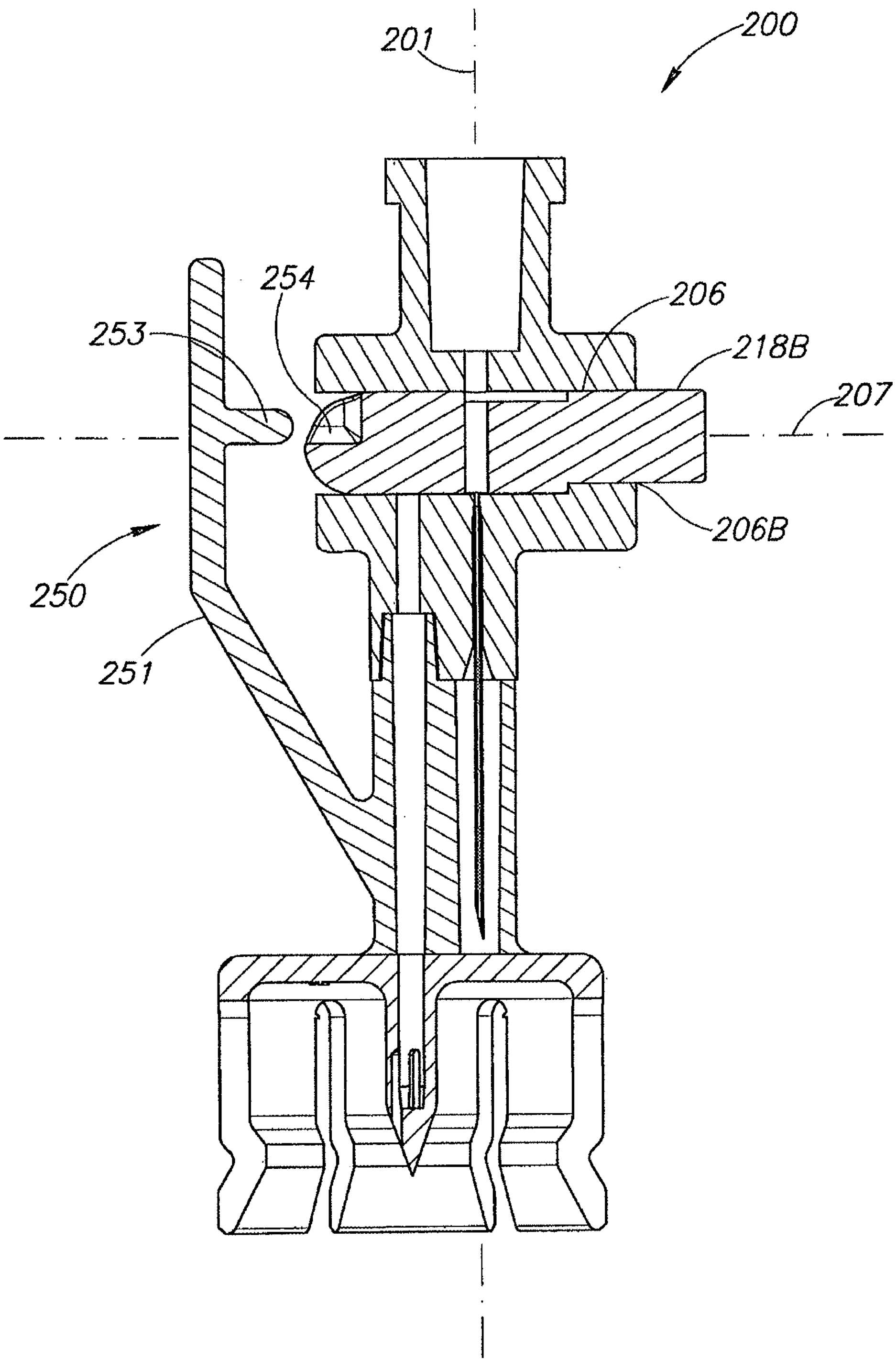
FIG. 13 is a longitudinal cross sections of FIG. 8's device along line D-D in FIG. 8 showing its flow control member in a second flow control position for liquid drug administration purposes subsequent to actuation of its actuating mechanism.

Inline Liquid Drug Medical Devices including a Manually Operated Actuating Mechanism with a Spring Leaf-Like Actuator and a Linear Displaceable Sliding Flow Control Member FIG. 8 shows the syringe 10, the vial 20 and an inline liquid drug medical device 200 for use with the syringe 10 and the vial 20.

FIGS. 9 to 13 show the inline liquid drug medical device 200 has a longitudinal device axis 201 and includes a housing 202 and a vial adapter 203 removably coupled on the housing 202 and detachable therefrom along a line of detachment co-directional with the device axis 201. The housing 202 includes a generally cylindrical central body 204 with a throughgoing bore 206 having a bore axis 207 transversely directed to the device axis 201 and having a proximal end 206A and a distal end 206B.

The housing 202 includes a syringe port 208 constituting a first port in flow communication with the bore 206 and a port manifold 209 on opposite sides of the central body 204. The syringe port 208 is co-directional with the device axis 201 and preferably co-axial therewith. The port manifold 209 includes a pair of opposite and parallel major surfaces 211 co-directional with the bore axis 207 and a pair of opposite minor end surfaces 212 for securing the vial adapter 203 onto the housing 202. The port manifold 209 includes the second port 213 and the third port 214 both in flow communication with the bore 206. The second port 213 and the third port 214 are co-directional with the device axis 201 and the third port 214 is preferably co-axial therewith. A center of the second port 213 is offset from the device axis 201 by a length L. The third port 214 is preferably fitted with a needle 216. The second port 213 is preferably recessed with respect to the third port 214 thereby forming a cavity 217 for sealingly coupling the vial adapter 203 to the housing 202.

The housing 202 includes a flow control member 218 for sliding linear movement along the bore 206 from an initial first flow control position for establishing flow communication between the first port 208 and the second port 213 to a subsequent second flow control position for establishing flow communication between the first port 208 and the third port 214. The bore 206 has a uniform cross section therealong except its distal end 206B which is formed with a platform 219 on the side of the port manifold 209 for acting as a stopper for stopping the sliding linear movement of the flow control member 218 at its second flow control position. The platform may be formed on the side of the syringe port 208.

The flow control member 218 has a proximal end 218A and a distal end 218B and a peripheral cylindrical surface 221. The flow control member 218 is shaped and dimensioned for sealing insertion in the throughgoing bore 206 and is longer than same such that its proximal end 218A protrudes from the proximal end 206A in its first flow control position (see FIG. 12) and its distal end 218B protrudes from the distal end 206B in its second flow control position (see FIG. 13).

The flow control member 218 includes a flow channel 222 co-directional with the device axis 201 and disposed toward the proximal end 218A. The flow channel 222 has a proximal end 223 and a distal end 224. The peripheral surface 221 is formed with a longitudinally directed flow cutout 226 and a second longitudinally directed cutout 227 on the opposite side to the flow cutout 226. The cutout 227 faces the port manifold 209 and is located towards the distal end 218B and defines an abutment surface 228 for abutting against the stopper 219 for stopping the flow control member 218 at its second flow control position.

The vial adapter 203 includes a skirt 230 with a top surface 231 and downward depending flex members 232 for snap fitting onto a vial 20. The vial adapter 203 includes an elongated upright stem 233 terminating in a bifurcated tip 234 with a pair of opposite and parallel spaced apart inside surfaces 236 for friction fitting onto the port manifold 209's major surfaces 211. The stem 233 includes a fluid conduit 237 with a proximal end 237A for sealing insertion in the cavity 217 for sealed flow communication with the second port 213 on coupling the vial adapter 203 on the housing 202. The fluid conduit 237 terminates at the distal end 237B fluidly connecting with a pointed cannula 241. The stem 233 also includes a blind needle bore 238 for receiving the needle 216 on coupling the vial adapter 203 to the housing 202.

The vial adapter 203 is integrally formed with a manually operated actuating mechanism 250 for applying a linear actuation force LAF for imparting a linear displacement force LDF for sliding the flow control member 218 along the bore 206 from its first flow control position to its second flow control position. The actuating mechanism 250 is in the form of a hand operated upright spring leaf like actuator 251 attached towards the stem 233's base and having a free end 252 disposed opposite the flow control member's proximal end 218A. The actuator 251 has a pin 253 for sliding insertion into a recess 254 formed in the flow control member's proximal end 218A. The actuator 251 is preferably resiliently flexed from an initial position juxtaposed against the flow control member 218. The actuating mechanism 250 is preferably designed such that the pin 253 slides freely from the recess 254 on being released after being used to urge the flow control member 218 to its second flow control position to revert to its initial vertical position.

Figure 14D:
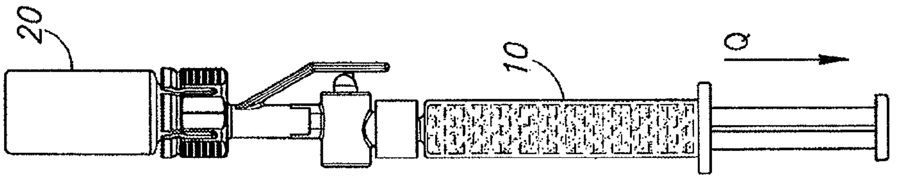
FIGS. 14A to 14H show the use of FIG. 8's device for liquid drug reconstitution and administration purposes.
Figure 14C:
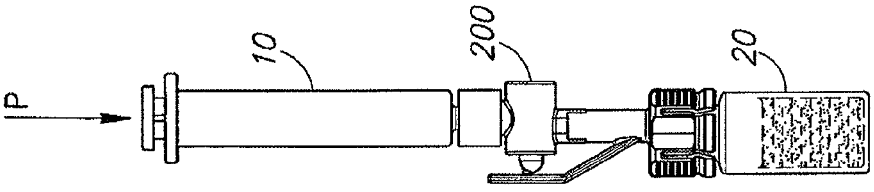
Figure 14B:
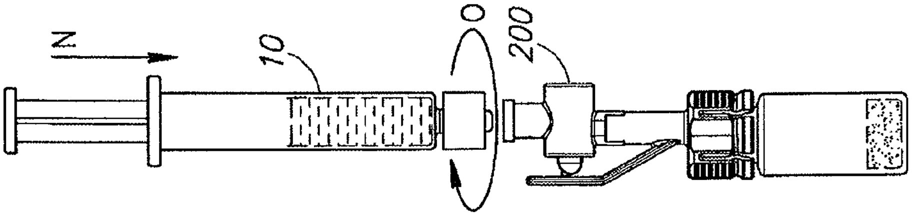
Figure 14A:
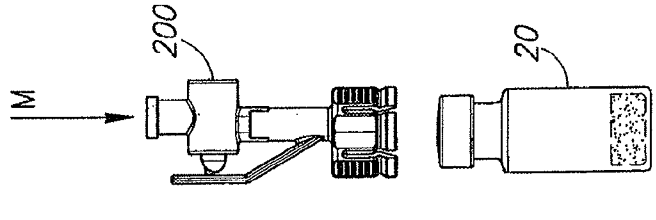

The use of the inline liquid drug medical device 200 for liquid drug reconstitution and administration as shown in FIGS. 14A to 14H is as follows:

FIG. 14A shows the device 200 is in its initial first flow control position for liquid drug reconstitution and a user mounting the device 200 on a vial 20, as indicated by arrow M.

FIG. 14B shows the user approximating the syringe 10 towards the device 200, as indicated by arrow N, and screw threading the syringe 10 onto the device 200, as indicated by arrow O.

FIG. 14C shows the user injecting the syringe's contents into the vial 20, as indicated by arrow P. The user agitates the assemblage for reconstituting the liquid drug.

FIG. 14D shows the user inverting the assemblage and aspirating the reconstituted liquid drug contents into the syringe 10, as indicated by arrow Q.

Figure 14H:
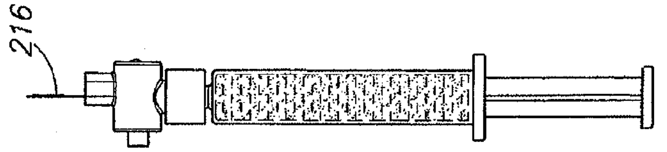
Figure 14G:
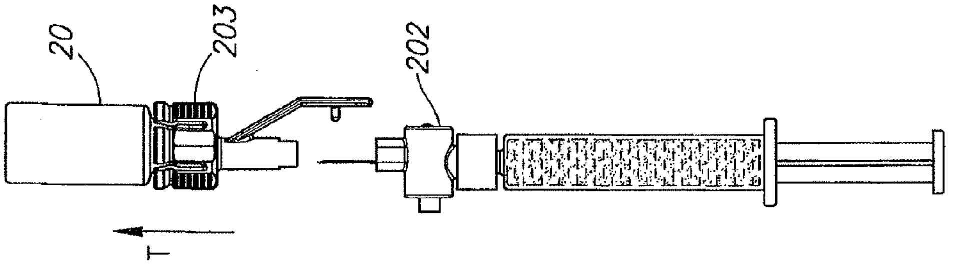
Figure 14F:
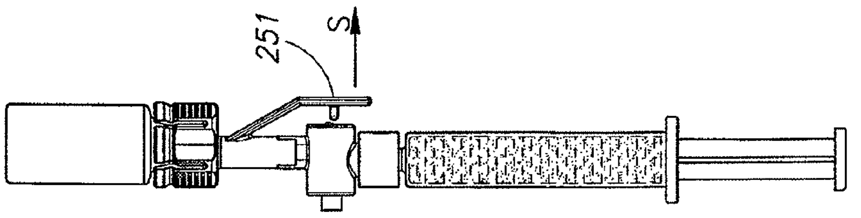
Figure 14E:
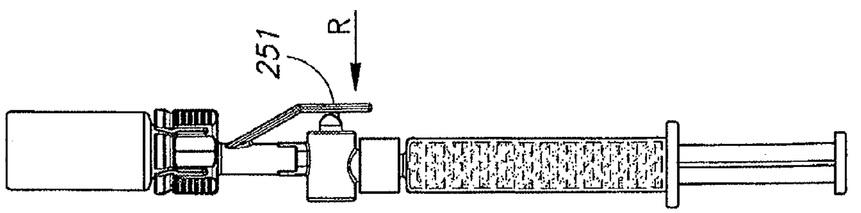

FIG. 14E shows the user depressing the hand operated actuator 239 to urge the flow control member 218 to its subsequent second flow control position in which the syringe port 208 is in flow communication with the third port 214, as indicated by arrow R.

FIG. 14F shows the user releasing the hand operated actuator 251 which reverts to its pre-depressed position, as indicated by arrow S. Optionally, for this step and the following steps, the user inverts the assemblage so that the syringe 10 is up and the vial 20 is down.

FIG. 14G shows the user pulling the vial adapter 203 with the spent vial 20 from the housing 202 for exposing the needle 216, as indicated by arrow T, thereby enabling administration of the liquid drug (see FIG. 14H).

Figure 15:
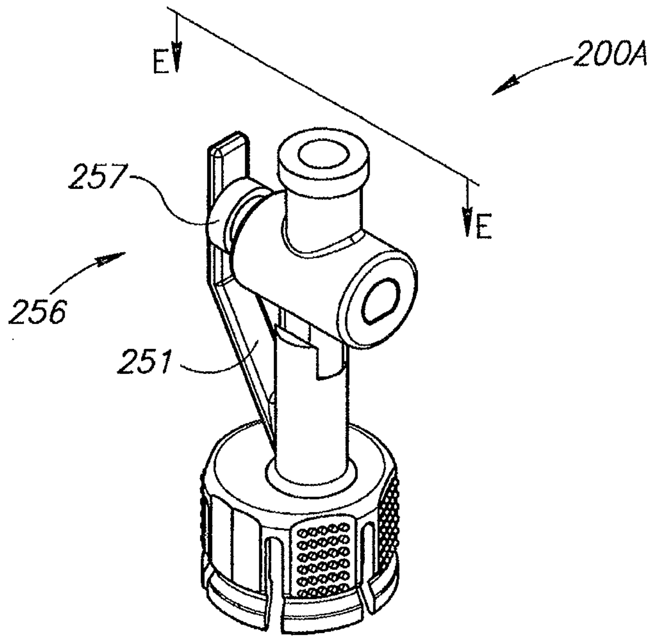
FIG. 15 is a pictorial representation of another embodiment of FIG. 8's device including a linear displaceable sliding flow control member in a first flow control position for liquid drug reconstitution purposes.
Figure 16:
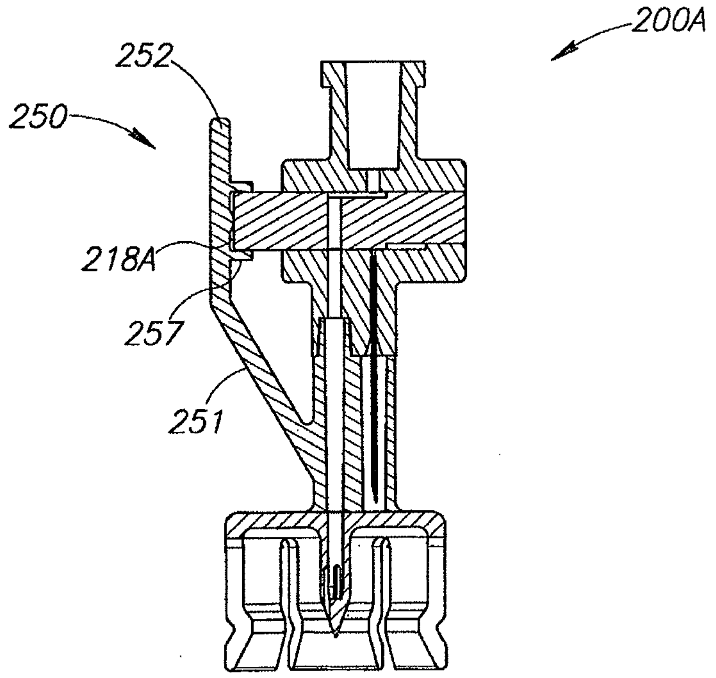
FIG. 16 is a longitudinal cross section of FIG. 15's device along line E-E in FIG. 15.

FIGS. 15 and 16 show an inline liquid drug medical device 200A similar in construction to the device 200 and therefore similar parts are likewise numbered. The device 200A differs from the device 200 insofar the former 200A includes an engagement mechanism 256 in which the free end 252 is formed with an annular flange 257 for engaging the proximal end 218A.

Figure 17:
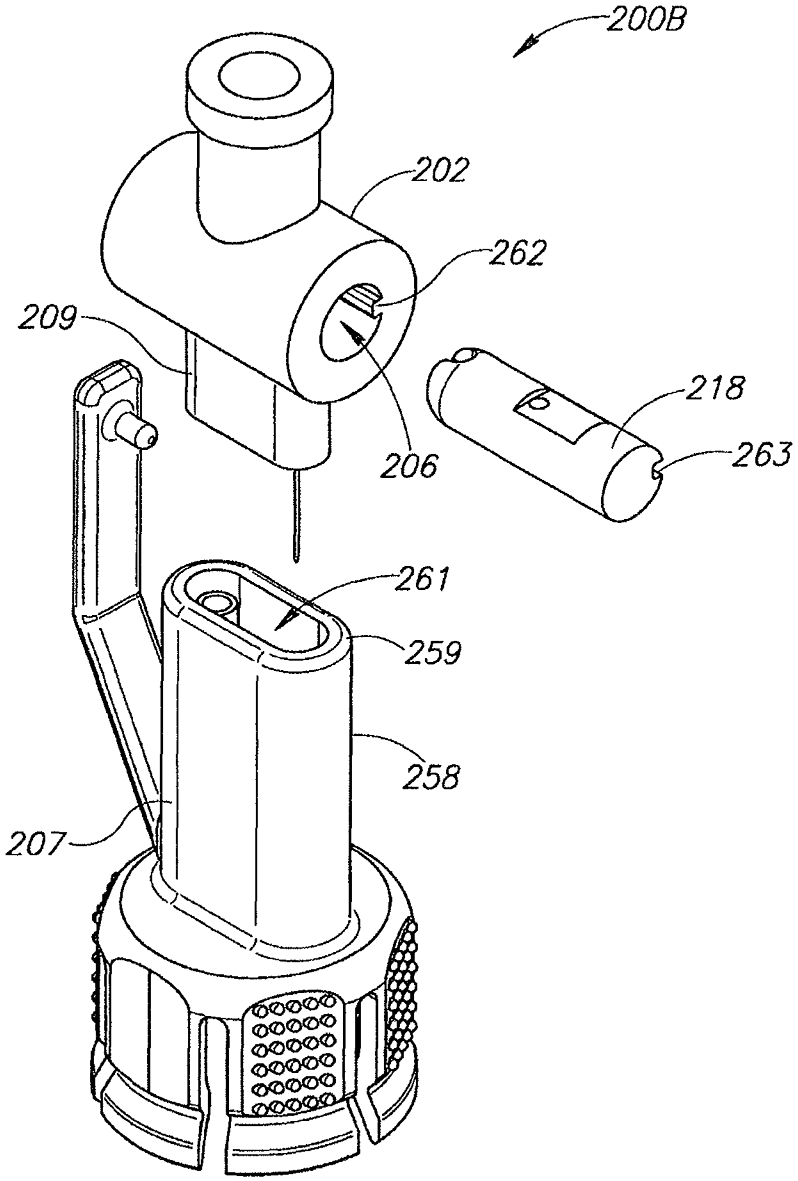
FIG. 17 is a pictorial representation of yet another embodiment of FIG. 8's device with a vial adapter having an elliptically shaped stem and stem tip with a stem tip cavity.

FIG. 17 show an inline liquid drug medical device 200B similar in construction and operation to the device 200 and therefore similar parts are likewise numbered. The device 200B differs from the device 200 insofar the former 200B includes an elliptically shaped stem 258 and stem tip 259 with a stem cavity 261, and a bore 206 which is cylindrically shaped and includes a keyed protrusion 262 extending therealong for fitting into a groove 263 in the flow control member 218. The keyed protrusion 262 and the groove 263 are configured for preventing rotation of the flow control member 218 inside the bore 206.

While the invention has been described with respect to a limited number of embodiments, it will be appreciated that many variations, modifications, and other applications of the invention can be made within the scope of the appended claims.

We claim:

1. An inline liquid drug medical device for use with a source of physiological solution and a medicinal vessel for reconstitution and administration of a liquid drug, the device having a longitudinal device axis, and comprising:

(a) a housing having a first port for fluid connection with the source of physiological solution, a second port for fluid connection with the medicinal vessel, a third port for liquid drug administration, said first port, said second port and said third port being co-directional with the longitudinal device axis, and a bore transversely disposed with respect to the longitudinal device axis and in flow communication with said first port, said second port and said third port;

(b) a flow control member linearly displaceable and slidable along said bore from a first flow control position to a second flow control position, wherein the flow control member directly establishes flow communication between said first port and said second port in the first flow control position for liquid drug reconstitution purposes, and movement of the flow control member from the first flow control position into the second flow control position directly establishes flow communication between said first port and said third port for liquid drug administration purposes;

(c) an actuating mechanism that is manually operated, having an initial liquid drug reconstitution position corresponding with said first flow control position and a subsequent liquid drug administration position corresponding to said second flow control position, said actuating mechanism applying a linear displace ent force for urging said flow control member to slide along said bore from said first flow control position to said second flow control position manually actuating said actuating mechanism from said initial liquid drug reconstitution position to said liquid drug administration position; and (d) a vial adapter for snap fitting onto the medicinal vessel and including a fluid conduit member with a proximal end in a flow communication with said port and a distal end in flow communication with a puncturing cannula extending into the medicinal vessel on the medicinal vessel's attachment to said vial adapter, and said vial adapter being removably attached to said housing along a line of detachment co-directional with the longitudinal device axis.

2. The device according, to claim 1, wherein said actuating mechanism rotates about an axis of rotation co-directional with the longitudinal device axis and has an internal cam surface bearing against said flow control member, said internal cam surface has a first separation S1 relative to said axis of rotation in said liquid drug reconstitution position and a second separation S2 relative to said axis of rotation in said liquid drug administration position where said second separation S2 is smaller than said first separation S1 whereby manual actuation of said actuating mechanism from said liquid drug reconstitution position to said liquid drug administration position applies a radial actuation force for imparting said linear displacement force.

3. The device according to claim 2, wherein said vial adapter is rotationally detachable from said housing and said rotational detachment simultaneously actuates said actuating mechanism from said liquid drug reconstitution position to said liquid drug administration position.

4. The device according to claim 2, wherein said axis of rotation is co-axial with the longitudinal device axis.

5. The device according to claim 2, wherein said flow control member includes a peripheral cylindrical surface with a longitudinal flow cutout in flow communication with said first port in said first flow control position and said second flow control position, and a flow channel for establishing flow communication between said flow cutout and said second port in said first flow control position, and said flow cutout and said third port in said second flow control position.

6. The device according to claim 5, wherein said flow channel is a lumen extending through said flow control member.

7. The device according to claim 5, wherein said flow channel is a semi-circular flow channel on said peripheral cylindrical surface.

8. The device according to claim 1, wherein said actuating mechanism includes a manually depressed actuator whereby manual actuation of said actuating mechanism applies a linear actuation force for imparting said linear displacement force.

9. The device according to claim 8, wherein said manually depressed actuator has a spring leaf like configuration including a first end resiliently flexibly mounted on said vial adapter and a second free end for urging said flow control member from said first flow control position to said second flow control position.

10. The device according to claim 8, wherein said flow control member includes a peripheral cylindrical surface with a longitudinal flow cutout in flow communication with said first port in said first flow control position and said second flow control position, and a flow channel for establishing flow communication between said flow cutout and said second port in said first flow control position, and said flow cutout and said third port in said second flow control position.

11. The device according to claim 10, wherein said flow channel is a lumen extending through said flow control member.

12. The device according to claim 10, wherein said flow channel is a semi-circular flow channel on said peripheral cylindrical surface.

13. The device according to claim 1, wherein said flow control member includes a peripheral cylindrical surface with a longitudinal flow cutout in flow communication with said first port in said first flow control position and said second flow control position, and a flow channel for establishing flow communication between said flow cutout and said second port in said first flow control position, and said flow cutout and said third port in said second flow control position.

14. The device according to claim 13, wherein said flow channel is a lumen extending through said flow control member.

15. The device according to claim 13, wherein said flow channel is a semi-circular flow channel on said peripheral cylindrical surface.

* * * * *